(12) United States Patent
John et al.

(10) Patent No.: US 11,179,439 B2
(45) Date of Patent: *Nov. 23, 2021

(54) METHODS AND COMPOSITIONS FOR PREVENTING AND TREATING DAMAGE TO THE HEART

(71) Applicants: MandalMed, Inc., San Francisco, CA (US); The Regents of the University of California, Oakland, CA (US)

(72) Inventors: Constance M. John, San Francisco, CA (US); Meenakshi Gaur, San Francisco, CA (US); Matthew L. Springer, San Francisco, CA (US); Xiaoyin Wang, San Francisco, CA (US)

(73) Assignees: MandalMed, Inc., San Francisco, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/445,086

(22) Filed: Jun. 18, 2019

(65) Prior Publication Data

US 2020/0246427 A1  Aug. 6, 2020

Related U.S. Application Data

(63) Continuation of application No. 15/666,456, filed on Aug. 1, 2017, now Pat. No. 10,369,195.

(60) Provisional application No. 62/342,704, filed on Aug. 9, 2016.

(51) Int. Cl.
*A61K 38/17* (2006.01)
*A61K 9/00* (2006.01)

(52) U.S. Cl.
CPC ........ *A61K 38/1732* (2013.01); *A61K 9/0019* (2013.01); *A61K 9/0021* (2013.01)

(58) Field of Classification Search
CPC .............. A61K 38/1732; A61K 9/0019; A61K 9/0021; A61P 9/04; A61P 9/10
See application file for complete search history.

(56) References Cited

U.S. PATENT DOCUMENTS

| | | |
|---|---|---|
| 5,789,166 A | 8/1998 | Bauer et al. |
| 5,923,419 A | 7/1999 | Thomas |
| 6,391,548 B1 | 5/2002 | Bauer et al. |
| 6,770,622 B2 | 8/2004 | Jarvis et al. |
| 9,272,014 B2 | 3/2016 | Chiriva-Internati et al. |
| 10,369,195 B2 | 8/2019 | John et al. |
| 2005/0032673 A1 | 2/2005 | John et al. |
| 2008/0226561 A1 | 9/2008 | Rittenhouse-Olson |
| 2015/0216931 A1* | 8/2015 | Chiriva-Internati ... A61K 31/69 424/9.2 |
| 2018/0042993 A1 | 2/2018 | John et al. |

FOREIGN PATENT DOCUMENTS

| | | | |
|---|---|---|---|
| WO | WO-0168123 A2 * | 9/2001 | ............. A61P 31/00 |
| WO | WO-2012/135528 A2 | 10/2012 | |
| WO | WO-2014/100703 A2 | 6/2014 | |

OTHER PUBLICATIONS

Wouter C. Meijers, Galectin-3 and post-myocardial infarction cardiac remodeling, European Journal of Pharmacology 763 (2015) 115-121.*
Richard Chin, Bruce Y. Lee, in Principles and Practice of Clinical Trial Medicine, 2008 10.5.2 Dosing Interval and Duration, pp. 2-3.*
Anroop B. Nair, A simple practice guide for dose conversion between animals and human, J Basic Clin Pharma 2016;7:27-31.*
Maarten Huismans, J Mol Cell Cardiol. Apr. 2016 ; 93: 149-155.*
Ahmad, N. et al. (Mar. 19, 2004, e-pub. Dec. 12, 2003). "Galectin-3 precipitates as a pentamer with synthetic multivalent carbohydrates and forms heterogeneous cross-linked complexes," *J Biol Chem.* 279(12):10841-10847.
Annapurna, A. et al. (2001). "Cardioprotective Effects of Acutely Administered Ramipril and Losartan on Myocardial Infarct Size In Cholesterol-Fed and Salt-fed Rats," *Indian Journal of Pharmacology.* 33(6):437-441.
Balan, V. et al. (Feb. 17, 2012, e-pub. Jan. 9, 2012). "Tyrosine-phosphorylated galectin-3 protein is resistant to prostate-specific antigen (PSA) cleavage," *J Biol Chem.* 287(8)5192-5198.
Balan, V. et al. (Oct. 2010). "Galectin-3: A novel Substrate for c-Abl Kinase," *Biochim Biophys Acta.* 1803(10):1198-1205.
Barondes, S. H. et al. (Feb. 25, 1994). "Galectins: A Family of Animal β-Galactoside-Binding Lectins," *Cell.* 76(4):597-598.
Bian, C. F. et al. (2011, e-pub. Sep. 20, 2011). "Structural Basis for Distinct Binding Properties of the Human Galectins to Thomsen-Friedenreich Antigen," *PLoS One* 6(9):e25007, 10 pages.
Borthwick, L.A. et al. (Jul. 2013, e-pub. Oct. 6, 2012). "Cytokine Mediated Tissue Fibrosis," *Biochim Biophys Acta.* 1832(7):1049-1060.
Bujak, M. et al. (Apr. 8, 2008). "Aging-Related Defects are Associated with Adverse Cardiac Remodeling in a Mouse Model of Reperfused Myocardial Infarction," *J Am Coll Cardiol.* 51 (14):1384-1392.
Burton, S. A. et al. (Jan. 2011, e-pub. Jun. 26, 2010). "Rapid Intradermal Delivery of Liquid Formulations Using a Hollow Microstructured Array," *Pharm Res.* 28(1):31-40.
Chaturvedi, R. et al. (Mar. 2008, e-pub. Aug. 17, 2007). "Tumor immunolocalization using [124]I-iodine-labeled JAA-F11 antibody to Thomsen-Friedenreich α-linked antigen," *Appl Radiat Isot.* 66(3):278-287.

(Continued)

*Primary Examiner* — James H Alstrum-Acevedo
*Assistant Examiner* — Erinne R Dabkowski
(74) *Attorney, Agent, or Firm* — Morrison & Foerster LLP

(57) ABSTRACT

Provided herein are methods and compositions for preventing and treating damage to the heart subsequent to myocardial infarction (MI) resulting from harmful fibrotic remodeling, thereby improving cardiac function and reducing mortality from subsequent heart failure.

16 Claims, 13 Drawing Sheets

Specification includes a Sequence Listing.

(56) References Cited

OTHER PUBLICATIONS

Choi, S. S. et al. (Nov. 2006). "Sustained Activation of Rac1 in Hepatic Stellate Cells Promotes Liver Injury and Fibrosis in Mice," *Hepatology* 44(5):1267-1277.

Clackson, T. et al. (May 1994). "In vitro Selection from Protein and Peptide Libraries," *Trends Biotechnol.* 12(5):173-184.

Cui, W. et al. (Sep. 2, 2011, e-pub. Jul. 27, 2011). "NOX1/nicotinamide Adenine Dinucleotide Phosphate, Reduced Form (NADPH) Oxidase Promotes Proliferation of Stellate Cells and Aggravates Liver Fibrosis Induced by Bile Duct Ligation," *Hepatology* 54(3):949-958.

Davidson, P. J. et al. (Jul. 2006, e-pub. Feb. 9, 2006). "Transport of Galectin-3 Between the Nucleus and Cytoplasm. I. Conditions and Signals for Nuclear Import," *Glycobiology* 16(7):602-611.

Davidson, P. J. et al. (May 2002). "Shuttling of Galectin-3 Between the Nucleus and Cytoplasm," *Glycobiology* 12(5):329-337.

De Boer, R. A. et al. (Jul. 2012, e-pub. Nov. 18, 2011). "The Fibrosis Marker Galectin-3 and Outcome in the General Population," *J Intern Med.* 272(1):55-64.

De Boer, R. A. et al. (Jun. 2014, e-pub. May 2, 2014). "Galectin-3: A Modifiable Risk Factor in Heart Failure," *Cardiovasc Drugs Ther.* 28(3):237-246.

De Torbal, A. et al. (Mar. 2006, e-pub. Feb. 14, 2006). "Incidence of Recognized and Unrecognized Myocardial Infarction in Men and Women aged 55 and Older: the Rotterdam Study," *Eur Heart J.* 27(6):729-736.

Dennis, J. W. et al. (2002). "UDP-N-acetylglucosamine:α-6-D-mannoside β1,6 N-acetylglucosaminyltransferase V (Mgat5) Deficient Mice," *Biochim Biophys Acta.* 1573:414-422.

Dörr, M. (Sep. 2010). "Silent Myocardial Infarction: The Risk Beyond the First Admission," 96(18):1434-1435.

Elena, C. et al. (Feb. 4, 2014, e-collection 2014). "Expression of Codon Optimized Genes in Microbial systems: Current Industrial Applications and Perspectives," *Front Microbiol.* 5(21):1-8.

F.D.A. 2005. Guidance for Industry: Estimating the Maximum Safe Starting Dose in Initial Clinical Trials for Therapeutics in Adult Healthy Volunteers. (Research, C. f. D. E. a. ed., Rockville, MD.

Frangogiannis, N. G. (Jan. 6, 2012). "Regulation of the inflammatory response in Cardiac Repair," *Circ Res.* 110(1):459-173.

Frangogiannis, N. G. (Aug. 2008). The Immune System and Cardiac Repair, *Pharmacol Res.* 58(2):88-111.

Frangogiannis, N. G. et al. (2002). "The Inflammatory Response in Myocardial infarction," *Cardiovasc Res.* 53:31-47.

Gaudin, J. C. et al. (2000). Nuclear Localisation of Wild Type and Mutant Galectin-3 In Transfected Cells, *Biol Cell.* 92:49-58.

Gibbons, R. J. (Oct. 19, 2004). "The Qualification of Infarct Size", *Journal of the Amencan College of Cardiology* 44(8):1533-1542.

Gonzalez G. et al. (Aug. 8, 2014). "Galectin-3 is essential for early wound healing and ventricular remodeling after myocardial infarction in mice," *International Journal of Cardiology* 176(3): 1423-1425.

Granovsky, M. et al. (Mar. 2000). Suppression of Tumor Growth and Metastasis in Mgat5-Deficient Mice. *Nat Med.* 6(3):306-312.

Grossman, W. (2000). "Defining Diastolic Dysfunction," *Circulation* 101:2020-2021.

Halimi, H. et al. (2014). "Glycan Dependence of Galectin-3 Self-Association Properties," *PLOS ONE.* 9(11):1-9.

Haudek, K. C. et al. (Feb. 2010, e-pub. Jul. 16, 2009). "Dynamics of Galectin-3 in the Nucleus and Cytoplasm," *Biochim Biophys Acta* 1800(2):181-189.

Heidenreich, P. A. (Mar. 1, 2011, e-pub. Jan. 24, 2011). "Forecasting the future of cardiovascular disease in the United States: a policy statement from the American Heart Association," *Circulation* 123:933-944.

Heimburg, J. et al. (Nov. 2006). Inhibition of Spontaneous Breast Cancer Metastasis by Anti-Thomsen-Friedenreich Antigen Monoclonal Antibody JAA-F11, *Neoplasia* 8(11):939-948.

Henderson, N. C. et al. (Jul. 2009). "The Regulation of Inflammation by Galectin-3," *Immunol Rev.* 230(1):160-171.

Hongo, M. et al. (1998). "Angiotensin II Blockade Followed by Growth Hormone as Adjunctive Therapy After Experimental Myocardial Infarction," *Journal of Cardiac Failure.* 4(3):213-224.

Hoyer, K. et al. (2004). "An Anti-Apoptotic Role for Galectin-3 in Diffuse Large B-Cell Lymphomas," *American Journal of Pathology.* 164(3):893-902.

Hsu, D. K. et al. (Jul. 15, 1992, e-pub. Jan. 21, 1992). "Biochemical and Biophysical Characterization of Human Recombinant IgE-Binding Protein, an S-Type Animal Lectin," *J. Biol. Chem.* 267(20):14167-14174.

Hu, K. et al. (1998). "Chronic effects of early started angiotensin converting enzyme inhibition and angiotensin AT1-receptor subtype blockade in rats with myocardial infarction: role of bradykinin," *Cardiovascular Research.* 39(2):401-412.

Hughes, R. C. (Dec. 6, 1999). "Secretion of the Galectin Family of Mammalian Carbohydrate-Binding Proteins," *Biochim Biophys Acta.* 1473(1):172-185.

Inohara, H. (Aug. 1, 1995). "Functional Evidence that Cell Surface Galectin-3 Mediates Homotypic Cell Adhesion," *Cancer Res.* 55:3267-3271.

Inohara, H. et al. (Dec. 15, 1998). "Galectin-3 Stimulates Cell Proliferation," *Exp Cell Res.* 245(2):294-302.

Jarvis, G. A. et al. (2012). "Galectin-3C: Human Lectin for Treatment of Cancer" Chapter 12 in *Galectins and Disease Implications for Targeted Therapeutics*, (Klyosov, A. A., and Traber, P. G. eds.), American Chemical Society, pp. 195-232.

Jia, W. et al. (May 2013). "Galectin-3 Accelerates M2 Macrophage Infiltration and Angiogenesis in Tumors," *Am J Pathol.* 182(5):1821-1831.

John, C. M. et al. (Jun. 2003). "Truncated galectin-3 inhibits tumor growth and metastasis in orthotopic nude mouse model of human breast cancer," *Clin Cancer Res.* 9:2374-2383.

John, C. SBIR Grant (2013) Protein inhibitor of galectin-3 to limit fibrosis after myocardial infarction. Located at: https://www.sbir.gov/sbirsearch/detail/678260 last visited on Nov. 3, 2017, 5 pages.

John, C.M. (2013). "Protein inhibitor of galectin-3 to limit fibrosis after myocardial infarction," *NIH*, 3 pages.

Jugdutt, B. I. (2013) "Regulation of Fibrosis After MI: Implications for Ventricular Remodeling," *Cardiac Remodeling* pp. 5:525-5:557.

Jugdutt, B. I. (Apr. 2008). "Aging and Remodeling During Healing of the Wounded Heart Current Therapies and Novel Drug Targets," *Curr Drug Targets* 9(4):325-344.

Jugdutt, B. I. (Apr. 9, 2009). "Limiting fibrosis after Myocardial Infarction," *Engl J Med.* 360:1567-1569.

Jugdutt, B. I. (Feb. 2009). "Role of Healing-Specific-Matricellular Proteins and Matrix Metalloproteinases in Age-Related Enhanced Early Remodeling After Reperfused STEMI in Dogs," *Mol Cell Biochem.* 322(1-2):25-36.

Jugdutt, B. I. et al. (Apr. 8, 2008). "Aging and Defective Healing, Adverse Remodeling, and Blunted Post-Conditioning in the Reperfused Wounded Heart," *J Am Coll Cardiol.* 51(14):1399-1403.

Jugdutt, B.I. (Sep. 16, 2003). "Ventricular Remodeling After Infarction and the Extracellular Collagen Matrix: When Is Enough Enough?," *Circulation* 108(11):1395-1403.

Kim, H-S. et al. (2013). "An Angiotensin Receptor Blocker Prevents Arrhythmogenic Left Atrial Remodeling in a Rat Post Myocardial Infarction Induced Heart Failure Model," *J Korean Med Sci.* 28()5:700-708.

Leening, M. J. et al. (2010, e-pub. May 18, 2010). "Unrecognised MI and Long-Term Risk of Heart Failure in the Elderly: The Rotterdam Study," *Heart* 96:1458-1462.

Lepur, A. et al. (Jul. 2012, e-pub. Mar. 17, 2012). "Galectin-3 Endocytosis by Carbohydrate Independent and Dependent Pathways in Different Macrophage Like Cell Types," *Biochim Biophys Acta.* 1820(7):804-818.

Li, S. Y. et al. (2006, Feb. 9, 2006). "Transport of Galectin-3 Between the Nucleus and Cytoplasm. II. Identification of the Signal for Nuclear Export," *Glycobiology* 16(7):612-622.

Liu, et al. (2009, e-pub. Dec. 19, 2009). "N-acetyl-seryl-aspartyl-lysyl-proline Prevents Cardiac Remodeling and Dysfunction Induced by Galectin-3, a Mammalian Adhesion/Growth-Regulatory Lectin", *Am J. Physiol Heart Circ Physiol* 296:H404-H412.

(56) References Cited

OTHER PUBLICATIONS

Liu, F. T. (Jan. 2005). "Galectins as Modulators of Tumour Progression," *Nat Rev Cancer* 5(1):29-41.
Liu, F. T. et al. (May 14, 1996). "Modulation of Functional Properties of Galectin-3 by Monoclonal Antibodies Binding to the Non-Lectin Domains," *Biochemistry* 35(19):6073-6079.
Liu, F. T. et al. (Oct. 4, 1995, e-pub. Jun. 23, 1995). "Expression and Function of Galectin-3, a β-Galactoside-Binding Lectin, in Human Monocytes and Macrophages," *Am J Pathol.* 147(4):1016-1028.
Lok, D. J. et al. (May 2010, e-pub. Feb. 4, 2010). "Prognostic Value of Galectin-3, a Novel Marker of Fibrosis, in Patients with Chronic Heart Failure: Data from the DEAL-HF Study," *Clin Res Cardiol* 99(5):323-328.
Lombardi, D. (2003). "Acceptance of External Infusion Pumps in Patients with Advanced Breast Cancer Receiving Continuous Infusion Fluorouracil," *Tumori.* 89:488-491.
Markowska, A. I. (Aug. 30, 2010). "Galectin-3 is an Important Mediator of VEGF- and bFGF-Mediated Angiogenic Response," *J Exp Med.* 207(9):1981-1993.
Massa, S.M. (Jan. 12, 1993). "L-29, an Endogenous Lectin, Binds to Glycoconjugate Ligands with Positive Cooperativity," *Biochemistry* 32(1):260-267.
McCullough, P.A. et al. (2011-2012). "Galectin-3: A Novel Blood Test for the Evaluation and Management of Patients With Heart Failure," *Rev Cardiovasc Med.* 12(4):200-210; Erratum in *Rev Cardiovasc Med.* 2012; 13(1):e52.
Mehul, B. et al. (1997). "Plasma Membrane Targetting, Vesicular Budding and Release of Galectin 3 from the Cytoplasm of Mammalian Cells During Secretion," *J Cell Sci.* 110:1169-1178.
Meijers, W.C. et al. (Apr. 2014, E-pub. Mar. 8, 2014). "The ARCHITECT Galectin-3 Assay: Comparison with other Automated and Manual Assays for the Measurement of Circulating Galectin-3 Levels in Heart Failure," *Expert Rev Mol Diagn.* 14(3):257-266.
Meijers, W.C. et al. (Jun. 19, 2015). "Galectin-3 and post-myocardial infarction cardiac remodeling," *European Journal of Pharmacology.* 763:115-121.
Menon, R.P. et al. (Sep. 1999). "Determinants in the N-Terminal Domains of Galectin-3 for Secretion by a Novel Pathway Circumventing the Endoplasmic Reticulum-Golgi Complex," *Eur J Biochem.* 264(2):569-576.
Messadi-Laribi, E. et al. (2007). "Tissue Kallikrein Is Involved in the Cardioprotective Effect of AT1-Receptor Blockade in Acute Myocardial Ischemia," *The Journal of Pharmacology and Experimental Therapeutics.* 323(1):210-216.
Mihardja, S.S. et al. (2010, E-pub. Apr. 28, 2010). "Targeted In Vivo Extracellular Matrix Formation Promotes Neovascularization in a Rodent Model of MI," *PLoS One* 5(4):e10384, 8 pages.
Mill, J. G. et al. (Oct. 2003). Spironolactone Prevents Cardiac Collagen Proliferation after MI in Rats, *Clin Exp Pharmacol Physiol.* 30(10)739-744.
Mirandola, L. (2011, E-pub. Jul. 13, 2011). "Galectin-3C Inhibits Tumor Growth and Increases the Anticancer Activity of Bortezomib in a Murine Model of Human Multiple Myeloma," PMC3135605, *PLoS One.* 6(7):e21811, 14 pages.
Moriki, T. et al. (Nov. 1999). "Protein Domain Mapping by Lambda Phage Display: The Minimal Lactose-Binding Domain of Galectin-3," *Biochem Biophys Res Commun.* 265(2):291-296.
Nahrendorf, M. et al. (Jun. 7-8, 2010). "Monocytes: Protagonists of Infarct Inflammation and Repair After MI," *Circulation* 121(22):2437-2445.
Nakahara, S. et al. (Oct. 15, 2006). "Characterization of the Nuclear Import Pathways of Galectin-3," *Cancer Res.* 66(20):9995-10006.
National Heart, L., and Blood Institute. 2008. NHLBI Financial Year 2008 Fact Book.
Nguyen, D.T. et al. (Oct. 2010, E-pub. Apr. 28, 2010). "Pirfenidone Mitigates Left Ventricular Fibrosis and Dysfunction After MI and Reduces Arrhythmias," *Heart Rhythm.* 7(10):1438-1445.
Nieminen, J. et al. (Jan. 12, 2007; E-pub. Nov. 2, 2006). "Visualization of Galectin-3 Oligomerization on the Surface of Neutrophils and Endothelial Cells Using Fluorescence Resonance Energy Transfer," *J Biol Chem.* 282(2):1374-1383.
Ochieng, J. et al. (Jan. 1998). "Modulation of the Biological Functions of Galectin-3 by Matrix Metalloproteinases," *Biochim Biophys Acta.* 1379(1):97-106.
Oda, Y. et al. (Mar. 15, 1991). "Human Breast Carcinoma cDNA Encoding a Galactoside-Binding Lectin Homologous to Mouse Mac-2 Antigen," *Gene* 99:279-283.
Openo, K. P. et al. (Mar. 15, 2000). "Galectin-3 Expression and Subcellular Localization in Senescent Human Fibroblasts," *Exp Cell Res.* 255(2):278-290.
Page, R. L. et al. (Sep. 2011). "A Call to Action: Responding to the Future Forecasting of Cardiovascular Disease in America," *Am Health Drug Benefits* 4(5):280-288.
Partridge, E.A. et al. (Oct. 1, 2004). "Regulation of Cytokine Receptors by Golgi N-Glycan Processing and Endocytosis," *Science* 306(5693):120-124.
Patten, R. D. et al. (Mar. 2009). "Small Animal Models of Heart Failure: Development of Novel Therapies, Past and Present," *Circ Heart Fail.* 2(2):138-144.
Roger, V. L., et al. 2012. Heart disease and stroke statistics—2012 update: a report from the American Heart Association. *Circulation.* 125:e2-e220.
Santiago, J.J. et al. (Jun. 2010, Apr. 9, 2010). "Cardiac Fibroblast to Myofibroblast Differentiation In Vivo and In Vitro: Expression of Focal Adhesion Components in Neonatal and Adult Rat Ventricular Myofibroblasts," *Dev Dyn.* 239(6):1573-1584.
Sato, S. et al. (Feb. 11, 1994). "Regulation of Secretion and Surface Expression of Mac-2, a Galactoside-Binding Protein of Macrophages," *J Biol Chem.* 269(6):4424-4430.
Seetharaman, J. et al. (May 22, 1998). "X-ray Crystal Structure of the Human Galectin-3 Carbohydrate Recognition Domain at 2.1-A Resolution," *J Biol Chem.* 273(21):13047-13052.
Shah, R. V. et al. (Aug. 2010, E-pub. Jun. 5, 2010). "Galectin-3, Cardiac Structure and Function, and Long-Term Mortality in Patients with Acutely Decompensated Heart Failure," *Eur J Heart Fail.* 12(8):826-832.
Sharma, U.C. et al. (Nov. 9, 2004, E-pub. Nov. 1, 2004). "Galectin-3 Marks Activated Macrophages in Failure-Prone Hypertrophied Hearts and Contributes to Cardiac Dysfunction," *Circulation* 110(19):3121-3128.
Sheifer, S.E. et al. (Nov. 6, 2001). "Unrecognized Myocardial Infarction," *Ann Intern Med.* 135(9):801-811.
Silvestre, J.S. et al. (1999). "Activation of cardiac aldosterone production in rat MI: effect of angiotensin II receptor blockade and role in cardiac fibrosis," *Circulation* 99:2694-2701.
Smith, G. P. et al. (Oct. 1991). "Surface Presentation of Protein Epitopes Using Bacteriophage Expression Systems," *Curr Opin Biotechnol.* 2(5):668-673.
Springer, M.L. et al. (Sep. 2005, E-pub. May 20, 2005). "Closed-Chest Cell Injections into Mouse Myocardium Guided by High-Resolution Echocardiography," *Am J Physiol Heart Circ Physiol.* 289(3):H1307-H1314.
Takagawa, J. et al. (Jun. 2007, E-pub. Mar. 8, 2007). "Myocardial Infarct Size Measurement in the Mouse Chronic Infarction Model: Comparison of Area- and Length-Based Approaches," PMC2675697, *J Appl Physiol.* 102(6):2104-2111.
Tsai, T.H. et al. (2012, E-pub. Oct. 3, 2012). "Value and Level of Galectin-3 in Acute MI Patients Undergoing Primary Percutaneous Coronary Intervention," *J Atheroscler Thromb.* 19(12):1073-1082.
Van Den Brûle, F.A et al. (Jul. 20, 2000). "Alteration of the Cytoplasmic/Nuclear Expression Pattern of Galectin-3 Correlates with Prostate Carcinoma Progression," *Int J Cancer.* 89(4):361-367.
Wang, X. et al. (Nov. 18, 2011, E-pub. Jun. 4, 2012). "Advanced Donor Age Impairs Bone Marrow Cell Therapeutic Efficacy for Cardiac Disease," PMC3366554, *J Tissue Sci Eng.* S3:002, 10pages.
Wang, X. et al. (Sep. 14, 2011, E-pub. May 13, 2012). "Donor Myocardial Infarction Impairs the Therapeutic Potential of Bone Marrow Cells by an Interleukin-1-Mediated Inflammatory Response," PMC3350804, *Sci Transl Med.* 3:100ra90, 20 pages.
Xue, H. et al. (2017). "The N-terminal tail coordinates with carbohydrate recognition domain to mediate galectin-3 induced apoptosis in T cells," *Oncotarget.* 8(30): 49824-49838.

(56) References Cited

OTHER PUBLICATIONS

Yang, R-Y. et al. (1996). "Expression of galectin-3 modulates T-cell growth and apoptosis," *Proc. Natl. Acad. Sci. USA.* 93(13):6737-6742.

Yeghiazarians, Y. et al. (Jul. 2009, Apr. 21, 2009). "Injection of Bone Marrow Cell Extract into Infarcted Hearts Results in Functional Improvement Comparable to Intact Cell Therapy," PMC2835212 *Mol Ther.* 17(7):1250-1256.

Yu, L. et al. (2013). "Genetic and Pharmacological Inhibition of Galectin-3 Prevents Cardiac Remodeling by Interfering With Myocardial Fibrogenesis", *Circ. Heart Fail* 6:107-117.

Zhang, Y. et al. (Jul.-Aug. 2011, E-pub. Jul. 29, 2010). "Timing of Bone Marrow Cell Therapy is More Important than Repeated Injections After Myocardial Infarction," *Cardiovasc Pathol.* 20(4):204-212.

International Preliminary Report on Patentability dated Mar. 23, 2021, for International Patent Application No. PCT/US2019/052020, filed Sep. 19, 2019, 8 pages.

International Preliminary Report on Patentability dated Feb. 21, 2019, for International Patent Application No. PCT/US2017/044905, filed Aug. 1, 2017, 8 pages.

International Search Report and Written Opinion of the International Searching Authority dated Nov. 27, 2019, for International Patent Application No. PCT/US2019/052020, 17 pages.

International Search Report and Written Opinion of the International Searching Authority dated Oct. 25, 2017, for International Patent Application No. PCT/US2017/044905, 16 pages.

\* cited by examiner

SEQUENCE LISTING

<160> NUMBER OF SEQ ID NOS: 12

<210> SEQ ID NO 1
<211> LENGTH: 250
<212> TYPE: PRT
<213> ORGANISM: Homo sapiens

<400> SEQUENCE: 1

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 2
<211> LENGTH: 818
<212> TYPE: DNA
<213> ORGANISM: Artificial Sequence
<220> FEATURE:
<223> OTHER INFORMATION: Synthetic construct

<400> SEQUENCE: 2
agcagccgtc cggagccagc caacgagcgg aaaatggcag acaattttc gctccatgat      60 gcgttatctg ggtctggaaa cccaaaccct caaggatggc ctggcgcatg ggggaaccag     120
cctgctgggg caggggcta cccaggggct tcctatcctg gggcctaccc cgggcaggca     180
cccccagggg cttatcctgg acaggcacct ccagcgcct accatggagc acctggagct     240
tatcccggag cacctgcacc tggagtctac ccagggccac ccagcggccc tggggcctac    300
ccatcttctg gacagccaag tgccccegga gcctacctg ccactggccc ctatggcgcc    360

```
cctgctgggc cactgattgt gccttataac ctgcctttgc ctgggggagt ggtgcctcgc    420
atgctcataa caattctggg cacggtgaag cccaatgcaa acagaattgc tttagatttc    480
caaagaggga atgatgttgc cttccacttt aacccacgct tcaatgagaa caacaggaga    540
gtcattgttt gcaatacaaa gctggataat aactggggaa gggaagaaag acagtcggtt    600
ttcccatttg aaagtgggaa accattcaaa atacaagtac tggttgaacc tgaccacttc    660
aaggttgcag tgaatgatgc tcacttgttg cagtacaatc atcgggttaa aaaactcaat    720
gaaatcagca actgggaat tctggtgac atagacctca ccagtgcttc atataccatg      780
atataatctg aaggggcag attaaaaaaa aaaacgga                             818
```

<210> SEQ ID NO 3
<211> LENGTH: 143
<212> TYPE: PRT
<213> ORGANISM: Artificial Sequence
<220> FEATURE:
<223> OTHER INFORMATION: Synthetic construct
<400> SEQUENCE: 3

```
Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

Pro Asn Ala Asn Arg Ile Ala Leu Asp Phe Gln Arg Gly Asn Asp Val
        35                  40                  45

Ala Phe His Phe Asn Pro Arg Phe Asn Glu Asn Asn Arg Arg Val Ile
    50                  55                  60

Val Cys Asn Thr Lys Leu Asp Asn Asn Trp Gly Arg Glu Glu Arg Gln
65                  70                  75                  80

Ser Val Phe Pro Phe Glu Ser Gly Lys Pro Phe Lys Ile Gln Val Leu
                85                  90                  95

Val Glu Pro Asp His Phe Lys Val Ala Val Asn Asp Ala His Leu Leu
            100                 105                 110

Gln Tyr Asn His Arg Val Lys Lys Leu Asn Glu Ile Ser Lys Leu Gly
        115                 120                 125

Ile Ser Gly Asp Ile Asp Ile Thr Ser Ala Ser Tyr Thr Met Ile
    130                 135                 140
```

<210> SEQ ID NO 4
<211> LENGTH: 432
<212> TYPE: DNA
<213> ORGANISM: Artificial Sequence
<220> FEATURE:
<223> OTHER INFORMATION: Synthetic construct
<400> SEQUENCE: 4

```
atgggcgccc ctgctgggcc actgattgtg cctataacc tgcctttgcc tgggggagtg      60
gtgcctcgca tgctcataac aattctgggc acggtgaagc ccaatgcaaa cagaattgct    120
ttagatttcc aaagagggaa tgatgttgcc ttccacttta acccacgctt caatgagaac    180
aacaggagag tcattgtttg caatacaaag ctggataata actggggaag gaagaaaga    240 cagtcggttt tcccatttga aagtgggaaa ccattcaaaa tacaagtact ggttgaacct    300
gaccacttca aggttgcagt gaatgatgct cacttgttgc agtacaatca tcgggttaaa    360
aaactcaatg aaatcagcaa actgggaatt tctggtgaca tagacctcac cagtgcttca    420 taccatga ta                                                          432
```

<210> SEQ ID NO 5
<211> LENGTH: 753
<212> TYPE: DNA
<213> ORGANISM: Artificial Sequence
<220> FEATURE:
<223> OTHER INFORMATION: Synthetic construct

<400> SEQUENCE: 5

```
atggcagata acttctcgct gcatgacgca ctgtcgggct cgggtaatcc gaatccgcag      60
ggctggccgg gcgcttgggg taatcaaccg gcaggtgccg gcggttatcc gggtgcttct     120
tatccgggcg cataccccggg tcaggctccg ccgggtgcat acccgggtca agcaccgccg     180
ggtgcatatc atggtgcacc gggtgcttac ccgggtgcac cggctccggg tgtgtatccg     240
ggtccgccgt caggcccggg tgcctacccg agctctggtc agccgtcggc accgggtgca     300
tatccggcaa cgggtccgta cggtgcaccg gcaggtccgc tgattgttcc gtataacctg     360
ccgctgccgg cggtgtggt tccgcgtatg ctgattacca tcctgggcac ggtcaaaccg     420
aacgctaatc gtattgcgct ggattttcaa cgcggtaacg acgtggcgtt tcatttcaac     480
ccgcgcttca tgaaaacaa tcgtcgcgtc atcgtgtgca ataccaaact ggataacaat     540
tggggccgtg aagaacgcca gagtgttttt ccgttcgaat ccggtaaacc gtttaaaatc     600
caagttctgg tcgaaccgga tcacttcaaa gtggccgtta atgacgcaca tctgctgcag     660
tataaccacc gtgtcaaaaa actgaatgaa attagtaaac tgggcatttc tggcgacatt     720
gacctgacct cggcgtccta cacgatgatt taa                                  753
```

<210> SEQ ID NO 6
<211> LENGTH: 432
<212> TYPE: DNA
<213> ORGANISM: Artificial Sequence
<220> FEATURE:
<223> OTHER INFORMATION: Synthetic construct

<400> SEQUENCE: 6

```
atgggtgcac cggcaggtcc gctgattgtt ccgtataacc tgccgctgcc gggcggtgtg      60
gttccgcgta tgctgattac catcctgggc acggtcaaac cgaacgctaa tcgtattgcg     120
ctggattttc aacgcggtaa cgacgtggcg tttcatttca acccgcgctt caatgaaaac     180
aatcgtcgcg tcatcgtgtg caataccaaa ctggataaca attggggccg tgaagaacgc     240
cagagtgttt ttccgttcga atccggtaaa ccgtttaaaa tccaagttct ggtcgaaccg     300
gatcacttca aagtggccgt taatgacgca catctgctgc agtataacca ccgtgtcaaa     360
aaactgaatg aaattagtaa actgggcatt tctggcgaca ttgacctgac ctcggcgtcc     420
tacacgatga tt                                                        432
```

<210> SEQ ID NO 7
<211> LENGTH: 143
<212> TYPE: PRT
<213> ORGANISM: Artificial Sequence
<220> FEATURE:
<223> OTHER INFORMATION: Synthetic construct

<400> SEQUENCE: 7

Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

```
Pro Asn Ala Asn Arg Ile Ala Leu Asp Phe Gln Arg Gly Asn Asp Val
            35                  40                  45

Ala Phe His Phe Asn Pro Arg Phe Asn Glu Asn Arg Arg Val Ile
 50                  55                  60

Val Cys Asn Thr Lys Leu Asp Asn Asn Trp Gly Arg Glu Glu Arg Gln
 65                  70                  75                  80

Ser Val Phe Pro Phe Glu Ser Gly Lys Pro Phe Lys Ile Gln Val Leu
                    85                  90                  95

Val Glu Pro Glu His Phe Lys Val Ala Val Asn Asp Ala His Leu Leu
                100                 105                 110

Gln Tyr Asn His Arg Val Lys Lys Leu Asn Glu Ile Ser Lys Leu Gly
                115                 120                 125

Ile Ser Gly Asp Ile Asp Leu Thr Ser Ala Ser Tyr Thr Met Ile
            130                 135                 140
```

<210> SEQ ID NO 8
<211> LENGTH: 143
<212> TYPE: PRT
<213> ORGANISM: Artificial Sequence
<220> FEATURE:
<223> OTHER INFORMATION: Synthetic construct

<400> SEQUENCE: 8

```
Gly Ala Pro Ala Gly Pro Leu Ile Val Pro Tyr Asn Leu Pro Leu Pro
 1               5                   10                  15

Gly Gly Val Val Pro Arg Met Leu Ile Thr Ile Leu Gly Thr Val Lys
                20                  25                  30

Pro Asn Ala Asn Arg Ile Ala Leu Asp Phe Gln Arg Gly Asn Asp Val
            35                  40                  45

Ala Phe His Phe Asn Pro Arg Phe Asn Glu Asn Arg Arg Val Ile
 50                  55                  60

Val Cys Asn Thr Lys Leu Asp Asn Asn Trp Gly Arg Glu Glu Arg Gln
 65                  70                  75                  80

Ser Val Phe Pro Phe Glu Ser Gly Lys Pro Phe Lys Ile Gln Val Leu
                    85                  90                  95

Val Glu Pro Glu His Phe Lys Val Ala Val Asn Asp Ala His Leu Leu
                100                 105                 110

Gln Tyr Asn His Arg Ala Lys Lys Leu Asn Glu Ile Ser Lys Leu Gly
                115                 120                 125

Ile Ser Gly Asp Ile Asp Leu Thr Ser Ala Ser Tyr Thr Met Ile
            130                 135                 140
```

<210> SEQ ID NO 9
<211> LENGTH: 24
<212> TYPE: DNA
<213> ORGANISM: Artificial Sequence
<220> FEATURE:
<223> OTHER INFORMATION: Synthetic construct

<400> SEQUENCE: 9
gttgaacctg aacacttcaa ggtt                                   24

<210> SEQ ID NO 10
<211> LENGTH: 27
<212> TYPE: DNA
<213> ORGANISM: Artificial Sequence
<220> FEATURE:
<223> OTHER INFORMATION: Synthetic construct

<400> SEQUENCE: 10

```
gacgacgaca agggcgcccc tgctggg                                          27

<210> SEQ ID NO 11
<211> LENGTH: 30
<212> TYPE: DNA
<213> ORGANISM: Artificial Sequence
<220> FEATURE:
<223> OTHER INFORMATION: Synthetic construct

<400> SEQUENCE: 11
gaggagaagc ccggtttata tcatggtata                                       30

<210> SEQ ID NO 12
<211> LENGTH: 24
<212> TYPE: DNA
<213> ORGANISM: Artificial Sequence
<220> FEATURE:
<223> OTHER INFORMATION: Synthetic construct

<400> SEQUENCE: 12
aatcatcggg ctaaaaaact caat                                             24
```

METHODS AND COMPOSITIONS FOR PREVENTING AND TREATING DAMAGE TO THE HEART

CROSS-REFERENCE TO RELATED APPLICATIONS

This application is a Continuation of U.S. application Ser. No. 15/666,456, filed Aug. 1, 2017, which claims the benefit of U.S. Provisional Application No. 62/372,704, filed Aug. 9, 2016, the disclosures of which are hereby incorporated by reference.

STATEMENT REGARDING FEDERALLY SPONSORED RESEARCH

This invention was made with government support under grant number R43 HL120645 and R44 AG054386, awarded by the National Institutes of Health. The government has certain rights to the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701642000101SEQLIST.TXT, date recorded: Jun. 11, 2019, size: 11 KB).

BACKGROUND OF THE INVENTION

Myocardial infarction (MI), commonly known as heart attack, occurs when blood flow to the heart is impeded by a clot or plaque in a blocked artery. The incidence of MI in the United States (US) is 610,000 new attacks and 325,000 recurrent attacks annually, approximately one every 34 seconds (80). The resulting condition of prolonged ischemia causes the cells of the heart to die, leading to loss of myocardium. The response of the body enhances excessive deposition of extracellular matrix (ECM) and formation of connective tissue or "fibrosis" in the heart. This provides structural support to the weakened ventricular wall (1) but the scar is not contractile. Regional inflammation and fibrosis occurs in response to the tissue injury to promote healing and repair of damaged tissues. However, excessive fibrosis is thought to be a major contributor to adverse remodeling that can further impair heart function, resulting in heart failure. Fibrosis is a feature of adverse remodeling in the heart post-MI, in some forms of heart failure, as well as many chronic human diseases (2), but to date there are few treatments that have direct effects on fibrosis.

The beating heart contracts and relaxes many times per minute, and healing of damage to the left ventricular (LV) chamber after an MI is necessary for the heart to continue to pump blood into the body (3). ECM remodeling is an essential step in response to heart injury because it provides structural integrity for the dying region of the myocardial wall. However, unchecked fibrosis can interfere with both systolic and diastolic function. Thus, reducing cardiac fibrosis to the appropriate extent and/or at the appropriate time during post-MI or post-injury remodeling is expected to improve long-term ventricular function so as to prevent development of heart failure and improve patient outcomes.

Recently implicated in the regulation of myofibroblast transformation and collagen deposition that play key roles in post-MI fibrosis a human lectin, galectin-3. Galectin-3 (FIG. 1) is unique among the galectins because in addition to the carbohydrate recognition domain on the carboxy-terminus, its amino-terminal domain also has specific functionality. The amino-terminal domain mediates oligomerization of galectin-3 when the carbohydrate recognition domain is bound to carbohydrates. This enables galectin-3 to cross-link carbohydrate-containing ligands and, thus, to modulate cell adhesion, migration, and signaling (15,16).

Upregulation of galectin-3 has been observed in hypertensive transgenic (mRen-2) rats (32). Galectin-3 levels were correlated with increased levels of ECM proteins such as collagen and fibronectin; galectin-3 co-localized to the sites of accumulation of the ECM proteins. Galectin-3 in the myocardium was higher in those animals that later progressed to heart failure compared to animals that did not. Furthermore, continuous intrapericardial administration of exogenous galectin-3 in healthy Sprague-Dawley rats induced cardiac fibrosis, remodeling, and dysfunction characterized by a decrease in left ventricular ejection fraction and fractional shortening (measures of pump efficiency), and an increase in lung:body weight ratio. Recombinant galectin-3 also was shown to stimulate cultured primary rat fibroblasts to proliferate and to produce collagen (32).

Galectin-3 levels in the blood have been established as a biomarker that has regulatory approval in the United States and Europe for use as an indicator for the risk of death in those with heart failure (35-38). A subset of patients with heart failure have elevated serum galectin-3 that is correlated with increased risk of death. These patients have a more progressive form of heart failure and worse prognosis (36,39).

Although there has been active research for decades focused on identifying molecular targets for improvement in healing and repair post-MI, reduction of adverse remodeling, and better therapeutic outcomes, this goal has still not been achieved (4,5). Discovery and development of a therapeutic agent that can effectively reduce excess fibrosis and adverse remodeling of the myocardium post-MI and in progressive heart failure is expected to have a major impact on morbidity and mortality associated with cardiovascular disease. Provided herein are methods and compositions for preventing and/or reducing excess fibrosis and adverse remodeling of the myocardium post-MI and in progressive heart failure.

SUMMARY

Provided herein are galectin-3 variants (collectively referred to herein interchangeably as "Gal-3C") that inhibit oligomerization of full-length galectin-3 for use in preventing and treating damage to the heart caused by cardiac fibrosis and fibrotic remodeling subsequent to myocardial infarction (MI), thereby improving cardiac function and reducing mortality from subsequent heart failure. Also provided are methods of making and using the Gal-3C variants provided herein.

In one aspect, described herein are methods of reducing fibrosis following myocardial infarction (MI) in a subject comprising administering to the subject an effective dose of Galectin-3C (Gal-3C). While not wishing to be bound by theory, the methods described herein are believed to reduce excess collagen deposition in the heart and therefore improve the functionality of the heart.

In another aspect, described herein are methods of reducing fibrosis in a subject with heart failure with elevated serum galectin-3 by administering to the subject an effective dose of Gal-3C. Such heart failure, for example, may arise from chronic hypertension.

In some embodiments of the above aspects, the Gal-3C is administered immediately following MI. In other embodiments, the Gal-3C is administered at least 2 weeks post MI. i.e., beginning no less than 2 weeks post-MI; beginning no less than 3 days post MI or heart failure; beginning no less than 8 days post MI or heart failure; beginning no less than 14 days post MI or heart failure; or beginning no less than 21 days post MI or heart failure.

In some embodiments that can be combined with any of the above embodiments, the subject is a human subject.

In some embodiments that can be combined with any of the above embodiments, the effective dose of Gal-3C is 0.15 mg/kg/day, 0.3 mg/kg/day, or 0.5 mg/kg/day.

In some embodiments that can be combined with any of the above embodiments, the Gal-3C is administered intravenously, intramuscularly, transdermally, or subcutaneously; administered intravenously with a pump; and/or in three divided doses.

DETAILED DESCRIPTION OF THE INVENTION

Definitions

Figure 1:
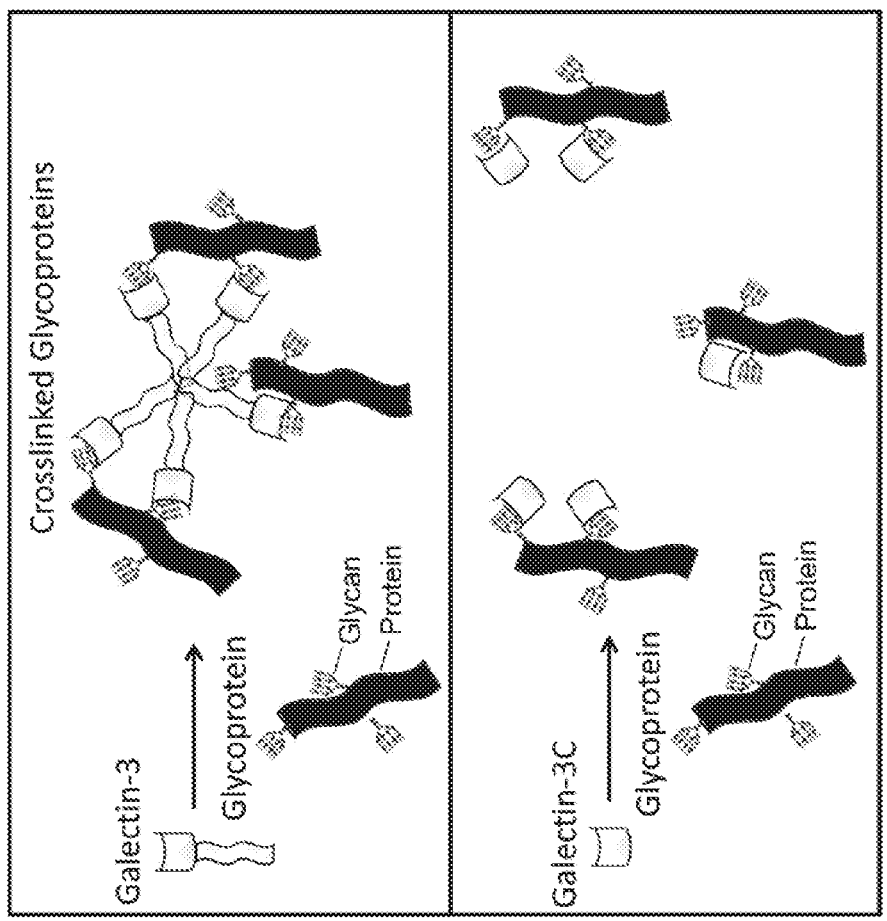
FIG. 1. A schematic (top) showing galectin-3 binding to the N-glycans of glyco-proteins and forming oligomers that result in glycoprotein clustering. Schematic (bottom) illustrating the binding of galectin-3C (Gal-3C) to N-glycans of glycoproteins that does not cause the formation of oligomers and does not cause clustering of the glycoproteins. Gal-3C inhibits the oligomerization induced by galectin-3 by binding to its carbohydrate ligands and thereby blocking its carbohydrate binding and preventing its oligomerization.

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as "consisting essentially of" a component, the composition may additionally contain any amount of pharmaceutically acceptable carriers, vehicles, or diluents and other such components which do not substantially affect the condition being treated.

An "effective amount" or "therapeutically effective amount" as used herein refers to an amount of therapeutic compound, administered to a subject, either as a single dose or as part of a series of doses, which is effective to produce or contribute to a desired therapeutic effect, either alone or in combination with another therapeutic modality. An effective amount may be given in one or more dosages.

The term "treating" as used herein, refers to retarding or reversing the progress of a condition, such as fibrosis. The term "treatment," as used herein, refers to the act of treating a condition, such as fibrosis.

The term "preventing" as used herein, refers to delaying the onset of, reduce the frequency of symptoms, or reduce the severity of symptoms associated with a condition, such as fibrosis.

A "subject" as used herein refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the subject is human.

The term "about" as used herein refers to the usual error range for the respective value readily known to the skilled person in this technical field. Reference to "about" a value or parameter herein includes (and describes) embodiments that are directed to that value or parameter per se.

For any of the structural and functional characteristics described herein, methods of determining these characteristics are known in the art.

Overview

As provided herein, Gal-3C N-terminally truncated variants (collectively referred to herein interchangeably as "Gal-3C" in the singular) are N-terminally truncated forms of full length galectin-3, lacking the amino-terminal domain but retaining carbohydrate binding ability. Gal-3C acts as a dominant negative inhibitor of galectin-3 by preventing the oligomerization of galectin-3 and its cross-linking of carbohydrate-containing ligands on cell surfaces and in the ECM.

The Gal-3C variants provided herein are useful in reducing or inhibiting fibrosis following MI in a subject. It is shown here that the delayed administration of Gal-3C after a MI is as efficacious in reducing damage and preserving cardiac function as early administration. Gal-3C is thus useful for preventing and treating damage to the heart caused by cardiac fibrosis and fibrotic remodeling subsequent to MI, thereby improving cardiac function and reducing mortality from subsequent heart failure. The Gal-3C variants are also useful for methods of reducing fibrosis in a subject with heart failure with elevated serum galectin-3.

Galectin-3 Variants to be Used in Methods Described Herein

In the some embodiments, the galectin-3 variant to be used in the methods described herein is a Gal-3C variant.

In some embodiments, Gal-3C comprises the 136, 137, 138, 139, 140, 141, or 142 carboxy-terminal amino acid residues of full length galectin-3 that suffice for carbohydrate binding (93). In one specific embodiment, Gal-3C comprises the 143 carboxy-terminal amino acid residues of full length galectin-3.

In some embodiments, Gal-3C comprises the sequence provided in SEQ ID NO: 3.

```
                                                          (SEQ ID NO: 3)
GAP AGPLIVPYNL PLPGGVVPRM LITILGTVKP NANRIALDFQ

RGNDVAFHFN PRFNENNRRV IVCNTKLDNN WGREERQSVF

PFESGKPFKI QVLVEPDHFK VAVNDAHLLQ YNIIRVKKLNE

ISKLGISGDI DITSASYTMI
```

In some embodiments, the Gal-3C sequence comprises a sequence having at least 70%, 75%, 80%, 85%, 90%, 95%, 96%, 97%, 98%, or even 99% identity to SEQ ID NO: 3 and retains the requisite carbohydrate binding ability.

Methods for Synthesis of Gal-3C

In some embodiments, the Gal-3C variants are derived by exhaustive digestion with collagenase of the full-length human galectin-3 protein (49) that comprises the amino acid sequence of SEQ ID NO: 1:

```
                                                                                    (SEQ ID NO: 1)
  1   MADNFSLHDA LSGSGNPNPQ GWPGAWGNQP AGAGGYPGAS YPGAYPGQAP PGAYPGQAPP

61   GAYPGAPGAY PGAPAPGVYP GPPSGPGAYP SSGQPSATGA YPATGPYGAP AGPLIVPYNL

121   PLPGGVVPRM LITILGTVKP NANRIALDFQ RGNDVAFHFN PRFNENNRRV IVCNTKLDNN

181   WGREERQSVF PFESGKPFKI QVLVEPDHFK VAVNDMILLQ YNHRVKKLNE ISKLGISGDI

241   DLTSASYTMI
```

In some embodiments, the Gal-3C variants are derived from the full length galectin-3 which is encoded by the human LGALS3 gene that is located on chromosome 14, locus q21-q22 with cDNA sequence (49).

In some embodiments, a cDNA sequence for producing a recombinant full length galectin-3 protein for deriving the Gal-3C variants comprises whole or part of the sequence shown below in SEQ ID NO: 2. In some embodiments, a cDNA sequence for producing a recombinant full length galectin-3 protein for deriving the Gal-3C variants comprises the nucleotide sequence of SEQ ID NO: 2 starting from the underlined ATG up to the underlined ATA.

In some embodiments the Gal-3C variants are derived from full length human, rat, mouse, swine, cow, horse, feline, or canine galectin-3.

In some embodiments, Gal-3C can be produced by cleavage of an intact galectin-3, for example, by prostate specific antigen.

In some embodiments, Gal-3C can be produced by exhaustive digestion of full-length galectin-3 with collagenase (17,41), and then purified by affinity chromatography on lactosyl-sepharose.

In some embodiments, Gal-3C is produced by providing a nucleic acid vector having a cDNA, for example the nucleic acid sequence of SEQ ID NO: 4. In some embodiments, the cDNA produces a Gal-3C, wherein the amino acid sequence of the produced Gal-3C comprises the sequence set forth in SEQ ID NO: 3. In some embodiments, the cDNA produces a Gal-3C, wherein the amino acid sequence of the produced Gal-3C comprises a sequence having at least 70%, 75%, 80%, 85%, 90%, 95%, 96%, 97%, 98%, or even 99% identity to SEQ ID NO: 3.

```
                                                       (SEQ ID NO: 4)
ATGGGCGCC CCTGCTGGGC CACTGATTGT GCCTTATAAC

CTGCCTTTGC CTGGGGGAGT GGTGCCTCGC ATGCTCATAA

CAATTCTGGG CACGGTGAAG CCCAATGCAA ACAGAATTGC
```

```
                                                                              (SEQ ID NO: 2)
  1   AGCAGCCGTC CGGAGCCAGC CAACGAGCGG AAAATGGCAG ACAATTTTTC GCTCCATGAT

61   GCGTTATCTG GGTCTGGAAA CCCAAACCCT CAAGGATGGC CTGGCGCATG GGGGAACCAG

121   CCTGCTGGGG CAGGGGGCTA CCCAGGGGCT TCCTATCCTG GGGCCTACCC CGGGCAGGCA

181   CCCCCAGGGG CTTATCCTGG ACAGGCACCT CCAGGCGCCT ACCATGGAGC ACCTGGAGCT

241   TATCCCGGAG CACCTGCACC TGGAGTCTAC CCAGGGCCAC CCAGCGGCCC TGGGGCCTAC

301   CCATCTTCTG GACAGCCAAG TGCCCCCGGA GCCTACCCTG CCACTGGCCC CTATGGCGCC

361   CCTGCTGGGC CACTGATTGT GCCTTATAAC CTGCCTTTGC CTGGGGGAGT GGTGCCTCGC

421   ATGCTCATAA CAATTCTGGG CACGGTGAAG CCCAATGCAA ACAGAATTGC TTTAGATTTC

481   CAAAGAGGGA ATGATGTTGC CTTCCACTTT AACCCACGCT TCAATGAGAA CAACAGGAGA

541   GTCATTGTTT GCAATACAAA GCTGGATAAT AACTGGGGAA GGGAAGAAAG ACAGTCGGTT

601   TTCCCATTTG AAAGTGGGAA ACCATTCAAA ATACAAGTAC TGGTTGAACC TGACCACTTC

661   AAGGTTGCAG TGAATGATGC TCACTTGTTG CAGTACAATC ATCGGGTTAA AAAACTCAAT

721   GAAATCAGCA AACTGGGAAT TTCTGGTGAC ATAGACCTCA CCAGTGCTTC ATATACCATG

781   ATATAATCTG AAAGGGGCAG ATTAAAAAAA AAAACGGA
```

```
TTTAGATTTC CAAAGAGGGA ATGATGTTGC CTTCCACTTT

AACCCACGCT TCAATGAGAA CAACAGGAGA GTCATTGTTT

GCAATACAAA GCTGGATAAT AACTGGGAA GGGAAGAAAG

ACAGTCGGTT TTCCCATTTG AAAGTGGGAA ACCATTCAAA

ATACAAGTAC TGGTTGAACC TGACCACTTC AAGGTTGCAG

TGAATGATGC TCACTTGTTG CAGTACAATC ATCGGGTTAA

AAAACTCAAT GAAATCAGCA AACTGGGAAT TTCTGGTGAC

ATAGACCTCA CCAGTGCTTC ATATACCATG ATA
```

In some embodiments, the cDNA (e.g. human gene) for full-length galectin-3 expression for deriving the Gal-3C variants, has been optimized for expression in *Escherichia coli*. In some embodiments, the parameters that can be optimized include the following: codon usage bias, GC content, CpG dinucleotides content, secondary structure of mRNA, cryptic splicing sites, premature PolyA sites, internal chi sites and ribosomal binding sites, negative CpG islands, RNA instability motif, repeat sequences (direct repeat, reverse repeat, and Dyad repeat), and restriction sites that may interfere with cloning. In some embodiments, the length of an optimized human galectin-3 sequence from which Gal-3C is derived is 753 base pairs with GC %:57.87. An example of the optimized gene with is shown in SEQ ID NO: 5.

```
                                                     (SEQ ID 5)
  1  ATGGCAGATA ACTTCTCGCT GCATGACGCA CTGTCGGGCT CGGGTAATCC GAATCCGCAG

61  GGCTGGCCGG GCGCTTGGGG TAATCAACCG GCAGGTGCCG GCGGTTATCC GGGTGCTTCT

121  TATCCGGGCG CATACCCGGG TCAGGCTCCG CCGGGTGCAT ACCCGGGTCA AGCACCGCCG

181  GGTGCATATC ATGGTGCACC GGGTGCTTAC CCGGGTGCAC CGGCTCCGGG TGTGTATCCG

241  GGTCCGCCGT CAGGCCCGGG TGCCTACCCG AGCTCTGGTC AGCCGTCGGC ACCGGGTGCA

301  TATCCGGCAA CGGGTCCGTA CGGTGCACCG GCAGGTCCGC TGATTGTTCC GTATAACCTG

361  CCGCTGCCGG GCGGTGTGGT TCCGCGTATG CTGATTACCA TCCTGGGCAC GGTCAAACCG

421  AACGCTAATC GTATTGCGCT GGATTTTCAA CGCGGTAACG ACGTGGCGTT TCATTTCAAC

481  CCGCGCTTCA ATGAAAACAA TCGTCGCGTC A TCGTGTGCAA TACCAAACTG GATAACAAT

541  TGGGGCCGTG AAGAACGCCA GAGTGTTTTT CCGTTCGAAT CCGGTAAACC GTTTAAAATC

601  CAAGTTCTGG TCGAACCGGA TCACTTCAAA GTGGCCGTTA ATGACGCACA TCTGCTGCAG

661  TATAACCACC GTGTCAAAAA ACTGAATGAA ATTAGTAAAC TGGGCATTTC TGGCGACATT

721  GACCTGACCT CGGCGTCCTA CACGATGATT TAA
```

In another embodiment Gal-3C is produced from a nucleic acid vector optimized for direct expression in *E. coli*, comprising the sequence designated as SEQ ID NO: 6.

```
                                                     (SEQ ID 6)
AT GGGTGCACCG GCAGGTCCGC TGATTGTTCC GTATAACCTG

CCGCTGCCGG GCGGTGTGGT TCCGCGTATG CTGATTACCA

TCCTGGGCAC GGTCAAACCG AACGCTAATC GTATTGCGCT

GGATTTTCAA CGCGGTAACG ACGTGGCGTT TCATTTCAAC

CCGCGCTTCA ATGAAAACAA TCGTCGCGTC A TCGTGTGCAA
```

```
TACCAAACTG GATAACAAT TGGGGCCGTG AAGAACGCCA

GAGTGTTTTT CCGTTCGAAT CCGGTAAACC GTTTAAAATC

CAAGTTCTGG TCGAACCGGA TCACTTCAAA GTGGCCGTTA

ATGACGCACA TCTGCTGCAG TATAACCACC GTGTCAAAAA

ACTGAATGAA ATTAGTAAAC TGGGCATTTC TGGCGACATT

GACCTGACCT CGGCGTCCTA CACGATGATT
```

Additional Gal-3C Variants

It is understood that amino acids may be substituted on the basis of side chain bulk, charge and/or hydrophobicity. Amino acid residues are classified into four major groups: acidic, basic, neutral/non-polar, and neutral/polar. In some embodiments, an acidic amino acid may be substituted by another acidic amino acid. In some embodiments, a basic amino acid may be substituted by another basic amino acid. In some embodiments, neutral/non-polar amino acid may be substituted by another neutral/non-polar amino acid. In some embodiments, neutral/polar amino acid may be substituted by another neutral/polar amino acid.

Amino acid residues can be further classified as cyclic or non-cyclic, aromatic or non-aromatic with respect to their side chain groups these designations being commonplace to the skilled artisan. In some embodiments, the following exemplary or preferred substitutions can be made to the amino acid sequences presented herein.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala | Leu |
| Phe | Leu | Ile, Val |
| Ile | Met, Ala, Phe | |

-continued

| Original Residue | Exemplary Conservative Substitution | Preferred Conservative Substitution |
|---|---|---|
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Tyr |
| Tyr | Trp, Phe, Thr, Ser | Phe |
| Val | Ile, Leu, Met, Phe | Leu, Ala |

In some embodiments, alanine scanning mutagenesis as described by Cunningham and Wells (1989) Science, 244: 1081-1085, can be utilized to introduce mutations to make Gal-3C variants.

In some embodiments, phage display of protein or peptide libraries provides a methodology for the selection of Gal-3C variants with improved affinity, altered specificity, or improved stability (52).

In some embodiments, modifications of a Gal-3C sequence include conserved mutation substitutions of one or more amino acids occurring between position 201 and 230 (where the Gal-3C comprises the carboxy terminal 143 amino acids of SEQ ID NO: SEQ ID NO: 1). Possible conserved mutation substitutions include, but are not limited to, the following, where the amino acid on the left is the original and the amino acid on the right is the substituted amino acid.

| | | |
|---|---|---|
| Val-202 | → | Ala |
| Val-204 | → | Ala |
| Glu-205 | → | Asp |
| Asp-207 | → | Glu |
| His-208 | → | Arg |
| Phe-209 | → | Leu |
| Val-211 | → | Ala |
| Ala-212 | → | Val |
| Asp-215 | → | Glu |
| Ala-216 | → | Val |
| His-217 | → | Arg |
| Tyr-221 | → | Phe |
| His-223 | → | Arg |
| Val-225 | → | Ala |
| Glu-230 | → | Asp |

In some embodiments, amino acid substitutions can be performed using a PCR-based site-directed mutagenesis kit.

In some embodiments, a Gal-3C variant is Asp-207→Glu and comprises the amino acid sequence designated as SEQ ID NO: 7, as follows:

(SEQ ID NO: 7)
GAP AGPLIVPYNL PLPGGVVPRM LITILGTVKP NANRIALDFQ

RGNDVAFHFN PRFNENNRRV IVCNTKLDNN WGREERQSVF

PFESGKPFKI QVLVEPEHFK VAVNDAHLLQ YNHRVKKLNE

ISKLGISGDI DLTSASYTMI.

In some embodiments, the Gal-3C sequence comprises a sequence having at least 70%, 75%, 80%, 85%, 90%, 95%, 96%, 97%, 98%, or even 99% identity to SEQ ID NO: 7 and retains the requisite carbohydrate binding ability.

In some embodiments, the cDNA produces a Gal-3C wherein the amino acid sequence of the produced Gal-3C comprises the sequence set forth in SEQ ID NO: SEQ ID NO: 7. In some embodiments, the cDNA produces a Gal-3C, wherein the amino acid sequence of the produced Gal-3C comprises a sequence having at least 70%, 75%, 80%, 85%, 90%, 95%, 96%, 97%, 98%, or even 99% identity to SEQ ID NO: 7.

In some embodiments, a Gal-3C variant is Val-225→Ala and comprises the amino acid sequence designated as SEQ ID NO: 8, as follows:

(SEQ ID NO: 8)
GAP AGPLIVPYNL PLPGGVVPRM LITILGTVKP NANRIALDFQ

RGNDVAFHFN PRFNENNRRV IVCNTKLDNN WGREERQSVF

PFESGKPFKI QVLVEPEHFK VAVNDAHLLQ YNHRAKKLNE

ISKLGISGDI DLTSASYTMI.

In some embodiments, the Gal-3C sequence comprises a sequence having at least 70%, 75%, 80%, 85%, 90%, 95%, 96%, 97%, 98%, or even 99% identity to SEQ ID NO: 8 and retains the requisite carbohydrate binding ability.

In some embodiments, the cDNA produces a Gal-3C wherein the amino acid sequence of the produced Gal-3C comprises the sequence set forth in SEQ ID NO: 8. In some embodiments, the cDNA produces a Gal-3C, wherein the amino acid sequence of the produced Gal-3C comprises a sequence having at least 70%, 75%, 80%, 85%, 90%, 95%, 96%, 97%, 98%, or even 99% identity to SEQ ID NO: 8.

Other Galectin-3 Variants

Other modifications and variations of galectin-3 for use in the methods described herein are possible. For example, full-length galectin-3 may instead be truncated at the C-terminus, producing a variant comprising the N-terminal residues of the galectin-3. It has been shown that both the C-terminal amino acids of galectin-3 comprising the carbohydrate binding domain (as described in detail herein) and the N-terminal oligomerization domain of galectin-3 (amino acids 1 to 107) act as inhibitors of the bioactivity of galectin-3 to induce angiogenesis and cancer cell migration in vitro (46). Galectin-3 can be endocytosed by cells by both carbohydrate and non-carbohydrate dependent mechanisms, the latter involving the non-carbohydrate recognition domain on the N-terminal part of galectin-3 (92). Thus the two truncated inhibitory forms of galectin-3, the 1-107 amino acids comprising the N-terminal non-carbohydrate recognition protein binding domain, and the 108-250 amino acids comprising the C-terminal carbohydrate recognition domain of galectin-3 would be expected to have differing degrees of endocytosis depending on the cell type and could have differing subcellular distribution. Since galectin-3 has different bioactivity in the nucleus, cytoplasm, and ECM, a therapy for treatment post-MI and for cardiac fibrosis in heart failure utilizing the C-terminally truncated variants or both domains of galectin-3 could be advantageous. The C-terminally truncated variants could be produced by one of normal skill in the art by cloning using the previously described methods (46).

Pharmaceutical Compositions

The present application provides compositions comprising the Gal-3C variants including pharmaceutical compositions comprising any one or more of the Gal-3C variants described herein with one or more pharmaceutically acceptable excipients. In some embodiments the composition is sterile. The pharmaceutical compositions generally comprise an effective amount of a Gal-3C composition.

The present application provides kits comprising any one or more of the Gal-3C variants described herein. In some embodiments, the kits further contain pharmaceutically acceptable excipients, an instruction manual or any combination thereof. In one specific embodiment, the kit comprises a pharmaceutical composition comprising any one or more of the Gal-3C compositions described herein, with one or more pharmaceutically acceptable excipients.

The present application also provides articles of manufacture comprising any one of the Gal-3C compositions or kits described herein.

Pharmaceutical composition embodiments for other galectin-3 variants are also provided.

Methods for Use

In one embodiment, provided herein is a method of reducing or inhibiting fibrosis/fibrotic remodeling that occurs after non-fatal MI and that can lead to heart failure. In some embodiments of the method, the occurrence of an MI can be used to identify patients that could benefit from Gal-3C treatment for the first application.

In another embodiment, provided herein is a method for the prevention and/or treatment of heart failure from other causes that is characterized by actively progressive fibrogenesis and elevated serum levels of galectin-3. In some variations, patients that would benefit from Gal-3C treatment for treatment of heart failure from other causes could be identified based on the serum levels of galectin-3.

In some embodiments, provided herein is a method of reducing or inhibiting fibrosis/fibrotic remodeling following MI in a subject comprising administering to the subject an effective dose of Gal-3C following MI. In some embodiments, provided is a method for reducing the size of a primary infarct scar or the extent of interstitial border zone fibrosis following MI comprising administering to the subject an effective dose of Gal-3C following MI. Also provided here is a method for improving the contractile function and hemodynamic parameters in a subject following MI comprising administering to the subject an effective dose of Gal-3C following MI.

Methods for using other galectin-3 variants are also provided.

Dosing

In some embodiments, for in vivo administration of the Gal-3C described herein, dosage amounts for humans based on use of the appropriate body surface area conversion factor (BSA-CF) may vary from about 0.25 mg/kg/day to about 0.35 mg/kg/day, from about 0.25 mg/kg/day to about 0.45 mg/kg/day, from about 0.15 mg/kg/day to about 0.35 mg/kg/day, from about 0.2 mg/kg/day to about 0.3 mg/kg/day, from about 0.2 mg/kg/day to about 0.4 mg/kg/day, from about 0.3 mg/kg/day to about 0.5 mg/kg/day, from about 0.15 mg/kg/day to about 0.45 mg/kg/day, or even from about 0.4 mg/kg/day to about 0.9 mg/kg/day depending partly upon differences in exposure due to the route of administration, age, gender, and other factors. For repeated administrations over several days or longer, depending on the severity of the disease or disorder to be treated, the treatment is sustained until a desired response is achieved.

Variable dosage regimens may be useful, depending on the route of administration, pharmacokinetics of Gal-3C in humans, and the desired exposure levels and duration of exposure desired. Dosing an individual continuously using a pump for systemic delivery or from one to twenty-one times a week is contemplated herein. In certain embodiments, dosing frequency is three times per day, twice per day, once per day, once every other day, once weekly, once every two weeks, once every four weeks, or longer.

It is noted that use of Gal-3C in the methods provided herein uses doses significantly higher than those used for the treatment of cancer (e.g. see U.S. Pat. No. 9,272,014).

Timing and Time Windows

Although most patients experiencing an MI will likely have several symptoms such as angina pectoris, some individuals with MI will have no or atypical symptoms and the MI may not be recognized immediately. Such MIs can be categorized as 'silent'. Accordingly, in some embodiments then provided herein is a method of inhibiting fibrosis following MI in a subject comprising administering to a subject an effective dose of Gal-3C, wherein the Gal-3C is administered post MI. In some embodiments, the subject is a human subject. In some embodiments, the Gal-3C is administered to a human subject beginning at least 0, 1, 2, 3, 4, 5, 6, 7, 8, 9, 10, 14, 21, 35, or even 40 days post MI, i.e., beginning no less than 0, 1, 2, 3, 4, 5, 6, 7, 8, 9, 10, 14, 21, 35, or even 40 days post MI. In some embodiments, the Gal-3C is administered to a human subject from 1-7, 5-11, 7-21, 14-28, 21-35, 28-42, 35-49, or 40-54 days post MI, i.e., beginning no less than 1-7, 5-11, 7-21, 14-28, 21-35, 28-42, 35-49, or 40-54 days post MI.

An advantage of delayed treatment beginning nearly a month or more after an MI in a human would be the longer window of time for initiation of therapy that could increase the possibility for identification and then benefit for silent MIs. Epidemiological studies in which MIs were defined by the presence of abnormal Q waves in an electrocardiogram (ECG) indicate that as many as 2-40% of MIs are not recognized and present a very significant risk factor for the development of subsequent heart failure (88-91).

Differences in species in the rate of healing and repair from MI on cellular and physiological level typically must be taken into account. The rate of healing and the degree of repair after MI also is affected by other variables such as the infarct size, whether there is reperfusion or not, and other cellular and molecular factors (3). Advanced age is correlated with impaired healing (5,85,86) and increased size of infarcts from MI (87). Previous studies have analyzed the rate of collagen deposition post-MI by measurement of hydroxyproline concentration in the infarct zone and have found significant differences between mice, rats, dogs, sheep and pigs, and humans (3). The time to reach a plateau in collagen deposition is significantly longer in larger animals. Maximal deposition post-MI is between 1-2 weeks in mice, 2-3 weeks in rats, 4-6 weeks in dogs, and in humans occurs between 8-12 weeks (3).

In some embodiments, collagen deposition is used as a biomarker. As provided herein, delayed treatment of rats beginning at 4 days post-MI would be approximately equivalent to initiation of treatment beginning at 21 days in swine and at 35 days in humans post-MI in terms of the proportion of total collagen deposited during healing and repair (3). Treatment with Gal-3C for 7 days, beginning at 4 days until 10 days post-MI in rats would be roughly equal to treatment for 14 days in humans (3). Therapeutic inhibition of fibrosis that is efficacious even when delayed for a significant period of time post-MI is advantageous because it might better enable fibrotic repair of the infarct and prevention of wall rupture than anti-fibrotic treatment that must be administered as soon as possible post-MI for effectiveness.

In some embodiments other factors important in healing from MI other than collagen deposition are taken into account when determining the timing of administration. Such factors include, but are not limited to the magnitude of the infarct, and the age of the individual. When the methods performed by those who are skilled in the art, results in animal studies such as those described in the Examples in the rat ischemia-reperfusion model of MI can serve as a guide for the use of Gal-3C as a therapeutic agent for post-MI remodeling or for progressive fibrosis in the treatment of heart failure.

Administration

In some embodiments, Gal-3C is administered intravenously, intramuscularly, subcutaneously, topically, transdermally, intraperitoneally, via secretion by implanted genetically-modified cells, by inhalation, intrathecally, intraventricularly, or intranasally. An effective amount of Gal-3C may be administered for the treatment or prevention of fibrosis/fibrotic remodeling/heart failure. The appropriate dosage of Gal-3C may be determined based on the type of fibrosis or extent of fibrosis to be treated, the particular variant of the Gal-3C, and the severity and course of the MI, the clinical condition of the individual, the individual's clinical history and response to the treatment, and the discretion of the attending physician.

In some embodiments, for example in hospitalized patients, solutions of Gal-3C could be continuously delivered intravenously (IV) by infusion using traditional IV bags in phosphate-buffered saline or normal saline. For ambulatory patients Gal-3C could be delivered IV with non-electronic elastomeric external (Infusor; Baxter Corporation) pumps such as are used for chemotherapeutic and anesthetic agents. Baxter's "Infusor" elastomeric pumps provide duration infusion times from 12 hours to 7 days, are available with 7 different volumes varying from 48-272 milliliters, and have no cords, batteries or IV poles. These lightweight pumps do not require programming and have silent operation.

Using the Seven-Day Infusor (2C1082KP), continuous infusion of therapeutic agents for periods or more than 9 months have been used clinically (83). The Seven Day Infusor has a 95 milliliter volume and can be used for 7-day continuous IV delivery, i.e., of approximately 12 milliliter per day or 0.5 milliliter per hour. Thus, to deliver 20 milligrams of Gal-3C per day to a 60 kilogram person for 7 days, a solution of 1.67 milligrams Gal-3C with 4 milligrams lactose per milliliter of PBS could be used in the Seven Day Infusor. To deliver 30 milligrams per day to a 90-kilogram person for 7 days, a solution of 2.5 milligrams Gal-3C with 5 milligrams of lactose per milliliter of phosphate buffered saline could be used in the Seven-Day Infusor.

Alternatively, Gal-3C can be delivered intradermally using the Hollow Microstructured Transdermal System (hTMS; 3M Company) for microneedle-based administration from 2-4 times daily. This is an integrated reservoir and infusion device that is designed for rapid delivery of liquid formulations of small molecules and biologics such as proteins and peptides. The 3M hMTS enables delivery of 0.5 to 2.0 milliliters over a few minutes (84). The single-use delivery system is formed by a 1 square centimeter array molded out of medical grade polymer and is designed for self-administration. Using the hMTS an approximately 20-milligram daily dose of Gal-3C could be administered as 3 divided doses in 24 hours. Each dose would be 6.75 milligrams of Gal-3C in a solution of 1.5 milliliters (4.5 milligrams per milliliter of Gal-3C) with 5 milligrams lactose per milliliter in phosphate-buffered saline. For a 90-kilogram person, an approximately 30 milligram daily dose could be administered as 3 divided doses in 24 hours. Each dose would be 10 milligrams of Gal-3C contained in a solution of 2 milliliters (5 milligrams per milliliter of Gal-3C) with 10 milligrams lactose per milliliter in phosphate-buffered saline.

Progress of the therapy can be monitored by conventional techniques and assays. The dosing regimen, including the variant of Gal-3C administered, can vary over time independently of the dose used.

Combination Therapies

In some embodiments, the Gal-3C is administered in combination with beta blockers, angiotensin-converting enzyme (ACE) inhibitors, MRAs (mineralocorticoid receptor antagonists), angiotensin receptor blocker (ARBs), and anticoagulant and/or anticlotting medications. Gal-3C can be administered when grafting an artery or vein from elsewhere in the body to bypass a blocked portion of a coronary artery.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Figure 2B:
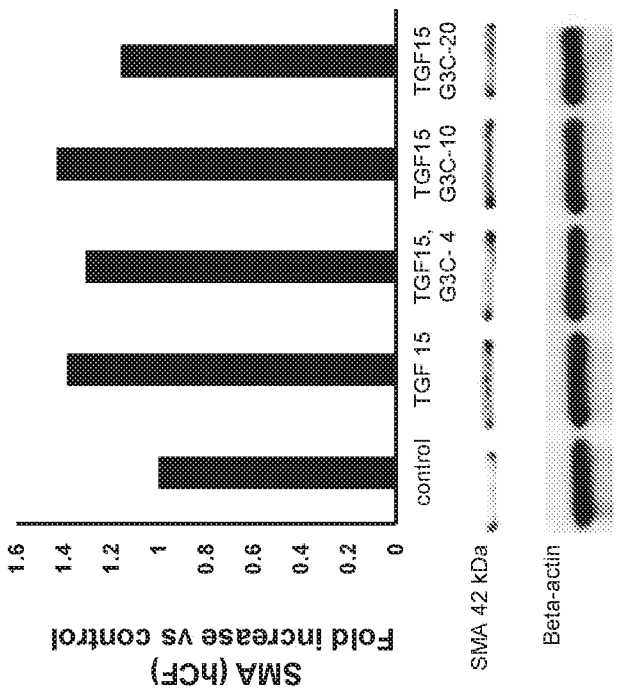
FIG. 2A and FIG. 2B. Immunoblots and densitometry of the immunoblots showing the effect of Gal-3C on TGFβ1-induced differentiation of cardiomyocytes in vitro. Gal-3C treatment (4-20 µg/ml) of human cardiomyocytes inhibited the differentiation to myofibroblasts induced by TGF1β (15 µg/ml) as shown by decreased expression of tensin-1 (A) and smooth muscle actin (B; SMA).
Figure 2A:
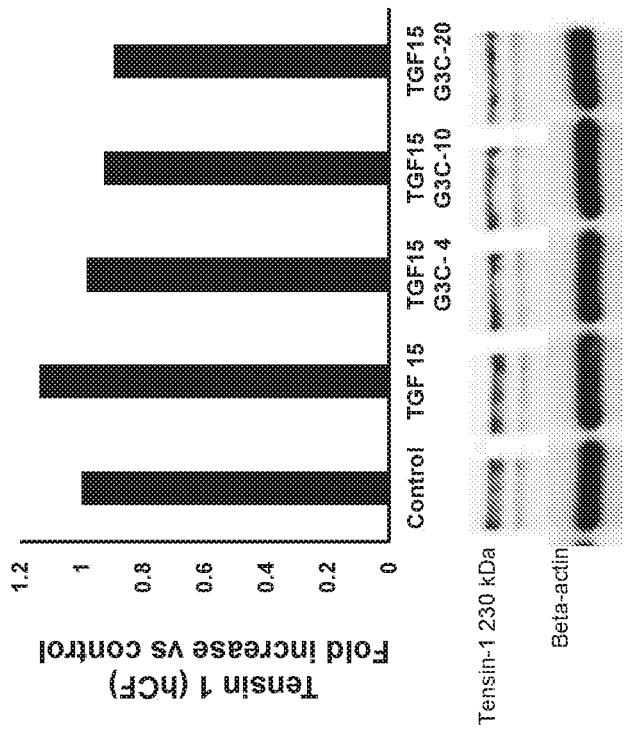

Example 1: Inhibition of TGF-β Induced Differentiation of Primary Cardiac Fibroblasts to Myofibroblasts In Vitro Galectin-3 was purified on lactosyl-sepharose from recombinant *E. coli* pelleted from 40 L of culture, collagenase digested, and then Gal-3C was isolated on lactosyl sepharose as previously described (41). Primary human cardiac fibroblasts (Cell Applications, San Diego, Calif.) were purchased and cultured as per the vendor's recommendations. 200,000 cells at passage 2-3 were cultured in 6-well plates until confluent, starved for 48 h and then induced to differentiate to myofibroblasts by treatment with 5 or 15 mg/ml TGFβ1 for 48-72 h. Varying concentrations of Gal-3C were also incubated with the cells. The cells were harvested, lysates prepared, and total protein quantified with a BCA assay (Pierce/Thermo). A total of 12 mg protein was analyzed per condition by immunoblots using primary Abs against smooth muscle actin (SMA) and tensin 1 (Sigma-Aldrich). The immunoblots (FIG. 2A and FIG. 2B) showed that treatment with Gal-3C inhibited expression of SMA and tensin 1 that are indicative of the differentiation of cardiac fibroblasts to myofibroblasts (60).

Example 2: Reduction of Fibrosis and Improved Left Ventricular Function after MI with Treatment Beginning Prior to MI Animal experiments to test the therapeutic potential of Gal-3C in the preservation of post-MI cardiac function were performed using surgical induction of MI in rodents and functional evaluation of treatment as previously described (61-66). To most accurately model cardiac damage experienced by MI patients, a well-established ischemia-reperfusion procedure was used in which the left anterior descending coronary artery (LAD) of rats was occluded for 25 min followed by restoration of blood flow (67). This standard MI model is more clinically relevant than permanent LAD ligation models because the reperfusion experienced after post-MI angioplasty not only limits the size of the infarct, but paradoxically introduces free radical damage, and is well validated as a model for post-MI heart failure experimental therapies (68).

Experiments were performed according to the UCSF guidelines for rodent survival surgery and the Guide for the Care and Use of Laboratory Animals of the US National Institutes of Health. Male Sprague-Dawley rats (age 10-12 weeks) were anesthetized with isoflurane (2%), received analgesics (buprenorphine (0.1 mg/kg), subcutaneous injection) pre- and post-operation, and underwent ischemia-reperfusion MI involving temporary (25 minutes) occlusion of the left anterior descending coronary artery (LAD) to produce regional moderate myocardial ischemia.

Briefly, rats were ventilated to a small animal volume-controlled ventilator (Harvard Rodent Ventilator, Model 683, South Natick, Mass.), and the heart was exposed via thoracotomy. Occlusion proceeds with a 7-0 nonabsorbable surgical suture passed under the LAD 2-3 mm from tip of the normally positioned left auricle and tied around a 1-mm section of PE-50 tubing, tightening with an artery clamp to temporarily occlude the LAD. After occlusion for 25 minutes, reperfusion was allowed to the formerly ischemic bed. The chest was then closed with removal of excess fluid and air from the chest cavity. All animals were monitored post-operation until they became ambulatory. The mortality during MI procedure was 12%.

A pilot dose-finding study was performed to determine Gal-3C levels reducing fibrosis, with collagen levels in heart tissue extracts as surrogate endpoints. It has been recommended to define dose in terms of difference in body surface area to determine the dose in one species equivalent to a dose in another species (69). Previously, a dose in mice of 30 µg/day of Gal-3C delivered using ALZET mini-osmotic pumps produced good efficacy in a xenograft model of human multiple myeloma (70). It was determined that an equivalent to the mouse dose for use in rats of 250-300 g/body weight based on $m^2$ of average body surface area of the two species as approximately 105 µg/day. Thus, 100, 200, 400, and 600 µg/day Gal-3C and vehicle control) doses were tested with small underpowered group sizes (n=2-3) in the pilot study. The mini-osmotic pumps (2ML1, ALZET, DURECT Corp.) were primed and implanted subcutaneously to deliver approximately 10 microliters of solution per hour, therefore, 240 microliters a day for 7 days. To achieve the desired dosages, the pumps were filled with solutions of Gal-3C at 0.0, 0.4, 0.8, 1.6, or 2.4 mg/ml in calcium/magnesium-free phosphate-buffered saline with lactose (8 mg/ml) as a stabilizer. After priming each pump was implanted subcutaneously immediately before surgical induction of MI, and the solutions were continuously infused via a jugular vein catheter.

Figure 3:
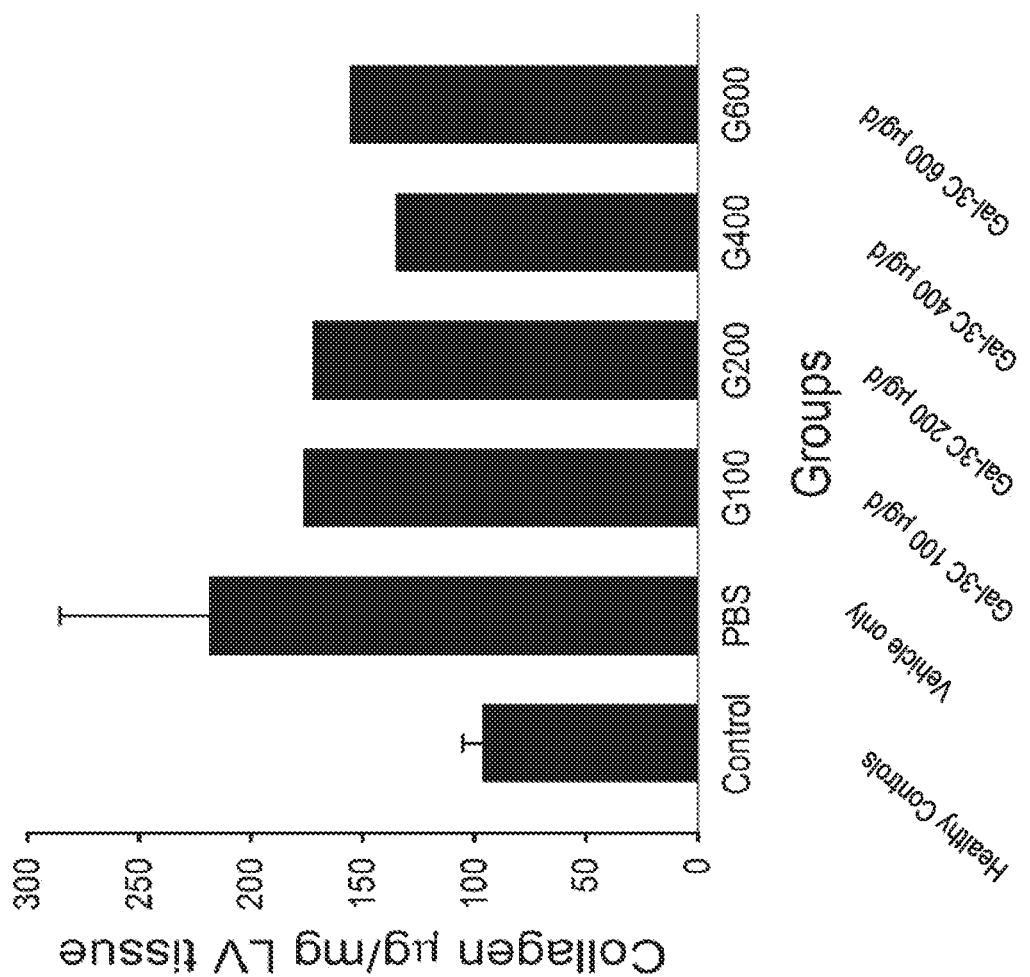
FIG. 3. A graph illustrating the effect of administration of Gal-3C from day 0 to day 6 post-MI on collagen deposition in the left ventricle. Collagen levels were assessed using a hydroxyproline assay of the heart tissue. Error bars=standard deviation (SD); n=3 for healthy controls, and vehicle only (PBS with lactose) controls; n=2 for Gal-3C treatment groups.

Rats were euthanized after 7 days and the left ventricle (LV) of the heart was homogenized (100 mg/100 ul in $H_2O$) with a Polytron (Brinkman PTA10TS). Analyses of hydroxyproline, an amino acid specifically contained in collagen, were performed as previously described with colorimetric detection at 588 nm (71,72) using a kit with hydrolysis of the tissue at 120° C. for 3 hours according to the instructions of the vendor (Biovision, Milpitas, Calif.). The results of the assay showed that the induction of MI increased the collagen levels in the LV by more than two-fold (FIG. 3). Treatment with Gal-3C reduced the collagen levels by approximately 20-35% with a trend to the greatest reduction observed at the 400 µg/day dose.

The highest dose, 600 µg/rat/day, and the lowest dose, 200 µg/rat/day, were chosen for continued study, representing approximately 2- and 5.5-fold higher doses based on body surface area of rats than was used in the multiple myeloma study of Gal-3C in mice (70). Groups of rats (n=10) were treated with low (200 µg/day) and high (600 µg/day doses of Gal-3C or with PBS-lactose (vehicle control) administered over 0-6 days post-MI ("early window"; primed pumps were implanted several minutes before the MI procedure on day 0). These groups were designed to be sufficiently powered to detect potentially statistically significant improvement from Gal-3C treatment.

Pre-filled and primed mini-osmotic pumps were implanted a few minutes before surgical induction of MI and Gal-3C treatment continued for 7 days (denoted as "early window") as in the pilot study described above. The effect of treatment on cardiac function was evaluated by serial echocardiography on day 0 pre-MI, 2 and 28 days post-MI, and LV pressure measurement at 28 days. For the early window, groups consisted of sham surgery with PBS, sham with 600 µg/day Gal-3C, MI with PBS, MI with 200 µg/day Gal-3C, and MI with 600 µg/day Gal-3C.

Figure 4:
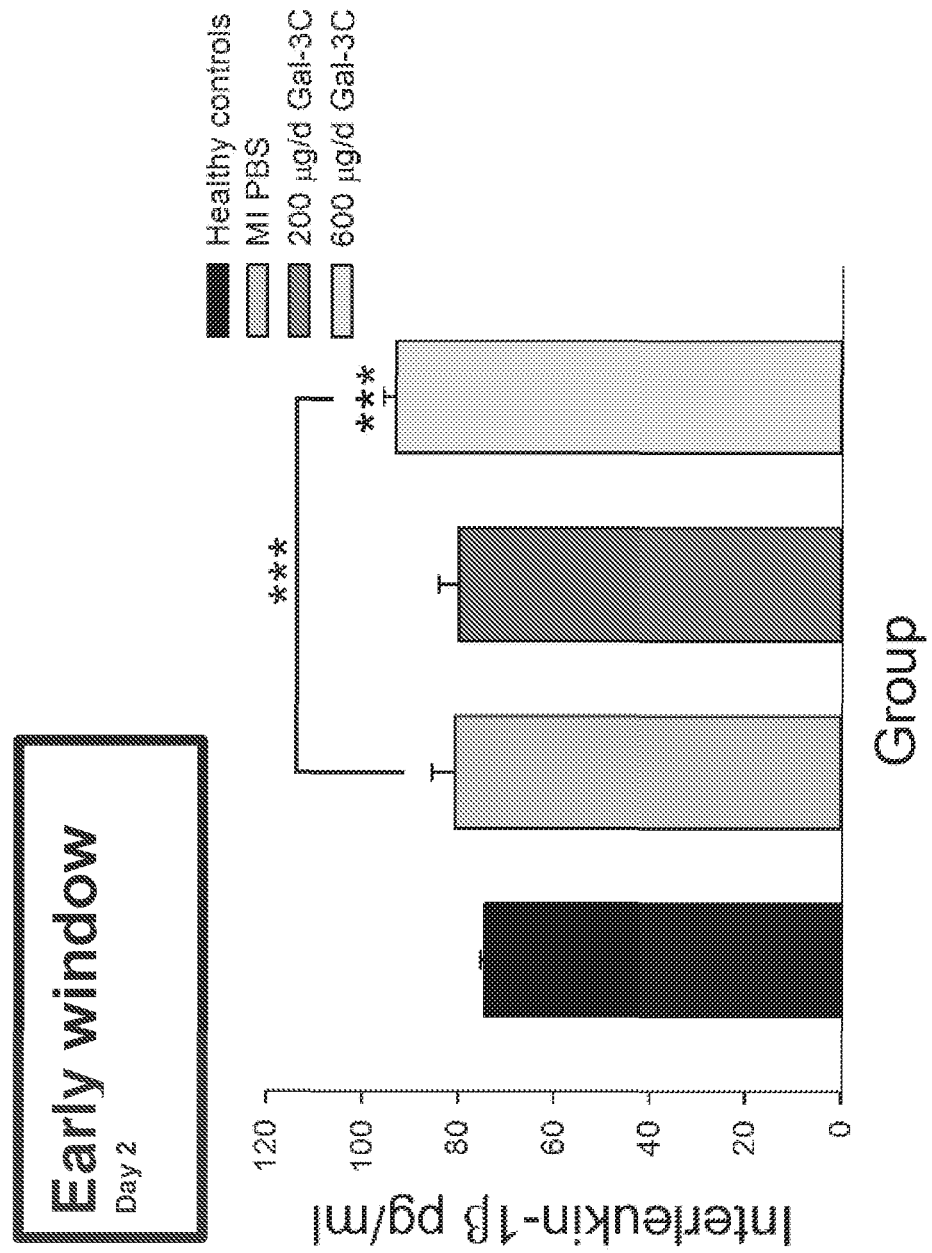
FIG. 4. Graph showing the effect of Gal-3C treatment (200 and 600 µg/day) of rats beginning just prior to ischemia-reperfusion injury on expression of interleukin (IL)-1β in the plasma at 2 days post-injury. IL-1β plasma levels were higher in Gal-3C treated groups subject to ischemia-reperfusion injury compared to sham healthy controls (P<0.001), and in injured groups treated with the higher 600 µg/day dose of Gal-3C compared to PBS-only controls (P<0.001). Error bars=SD; ***=P<0.001.
Figure 5:
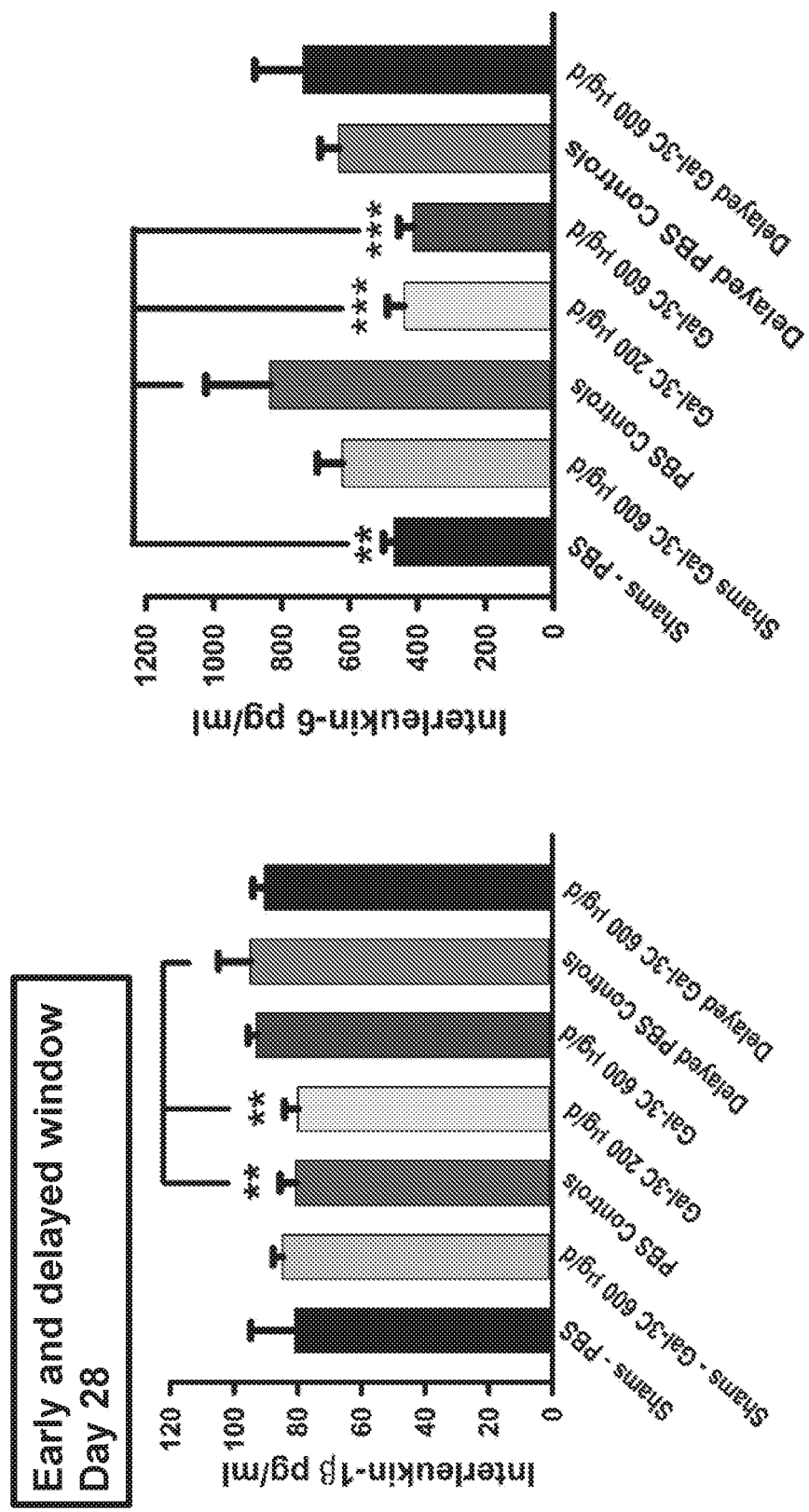
FIG. 5. Graphs of ELISAs of interleukin (IL)-1β and IL-6 levels in plasma of rats at day 28. Levels of IL-1β were higher in rats with PBS-only osmotic pumps implanted 4 days after injury (delayed window) compared to PBS-only controls and rats treated with 200 µg/day Gal-3C that had pumps implanted pre-injury. Levels of IL-6 were significantly higher in PBS controls compared to uninjured shams (shams—PBS) and compared to rats treated with Gal-3C 200 or 600 µg/day beginning before injury. Error bars=SD. =P<0.01, and *=P<0.001.

The levels of the inflammatory cytokines, interleukin (IL)-1β and IL-6, were determined in the plasma of control rats and rats with ischemia-reperfusion injury at 2 days (FIG. 4) and 28 days (FIG. 5) post-injury using ELISA kits according to the instructions of the vendor (Pierce ThermoFisher). The results showed that at 2 days post-MI (FIG. 4), there was a statistically significant increase in the levels of IL-1β in the animals receiving the higher dose of Gal-3C in the early window compared to the MI PBS-only controls. However, at 28 days, the levels of IL-1β were not significantly greater in the early window treated groups compared to the MI PBS-controls (FIG. 5 left). At 28 days, Gal-3C treatment in the early window, but not in the delayed window, significantly reduced the levels of IL-6 compared to PBS-only controls (FIG. 5 right).

Echocardiography revealed no significant functional changes over time in the sham groups (as expected; not shown), but MI groups receiving Gal-3C experienced profound benefit in left ventricular ejection fraction and end systolic volume (ESV) (FIG. 6 top panel, early window), indicating a preservation of contractile function. There was no benefit to LV end diastolic volume (EDV), a measure of wall compliance, at 28 days, but beneficial effects on EDV are more likely to manifest at a later time post-MI. Intraventricular pressure measurement detected relationships between groups that were consistent with reduction of function by MI and restoration by Gal-3C treatment (FIG. 7 top panel, early window) but the differences in the early window did not reach statistical significance.

Example 3: Reduction of Fibrosis and Improved Left Ventricular Function from Delayed Treatment Beginning 4 Days after MI In a subsequent experiment, the high dose Gal-3C and the PBS control were administered by Alzet pump over a delayed delivery window of from 4 days until 10 days post-MI (denoted as "delayed window") to rats that had been subjected to the same ischemia-reperfusion procedure as described in Example 2 above. Delayed treatment might better enable fibrotic repair of the infarct while preventing wall rupture. If efficacious, delayed treatment in the rats could be an indication that Gal-3C was acting to modulate the secondary reparative process that occurs later and over a longer time period than the acute or chronic inflammatory responses to MI, and could enable beneficial treatment of so-called "silent MIs" that sometimes are not detected for days or weeks after occurrence. In addition, beneficial results from delayed treatment could be indicative of the ability of the Gal-3C treatment to be efficacious for heart failure in which the process of fibrosis is ongoing and may be already advanced, and also could be evidence that Gal-3C treatment may have some ability to reverse fibrosis after it has occurred. The delayed window also avoided the pre-treatment resulting from the early window timing, which would have weaker clinical relevance.

Trends to greater improvement were obtained in treatment of animals with 600 µg/day Gal-3C compared to 200 µg/day in hemodynamic parameters (mean ABP, and dp/dt max and min, FIG. 7, top panel), Therefore, for the delayed window, treatment with 600 µg/day Gal-3C was evaluated using the same protocol as described above but with implantation of the mini-osmotic pumps and treatment with Gal-3C or vehicle-only beginning 4 days post-MI.

Figure 6:
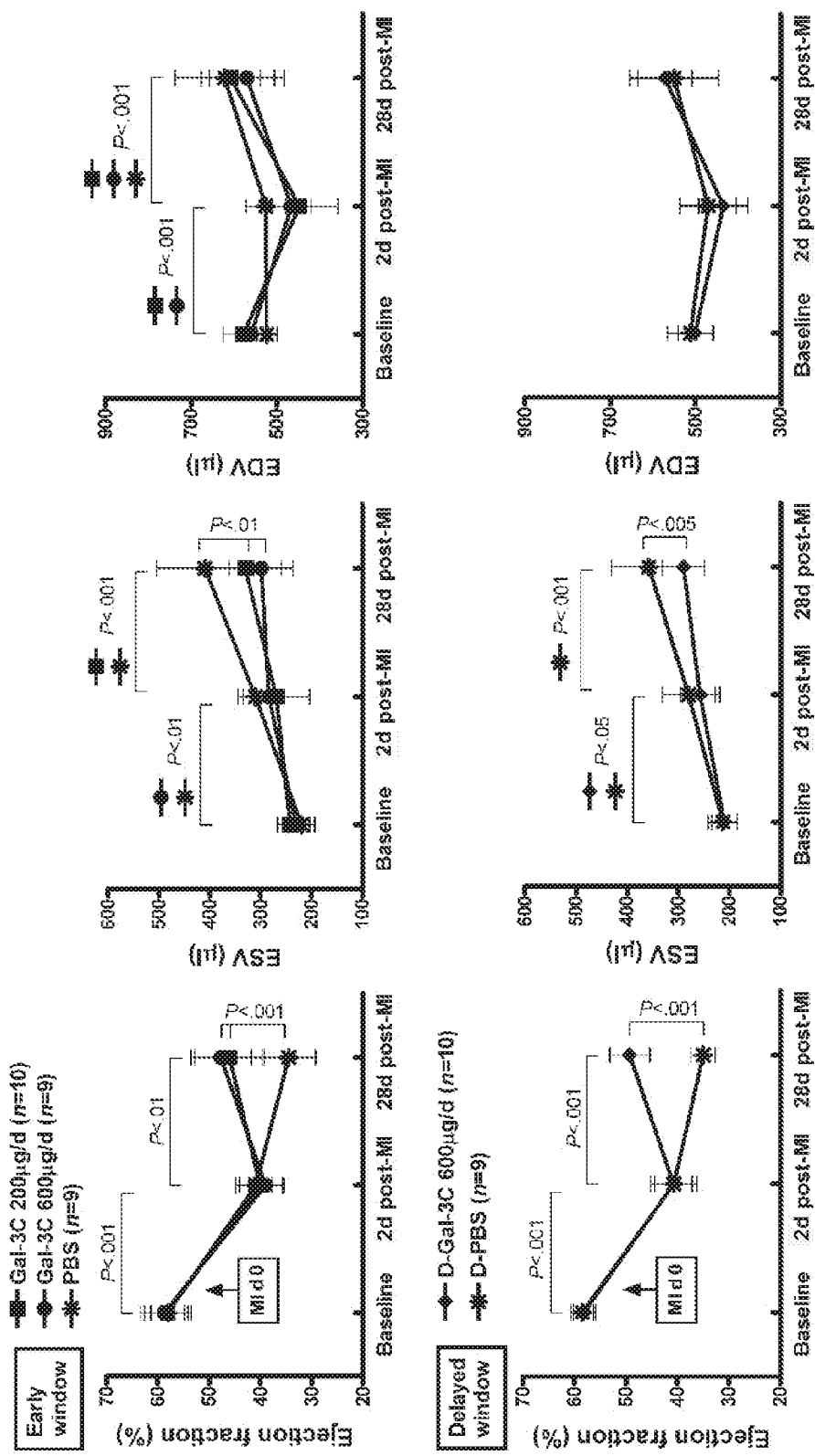
FIG. 6. Graphs showing the therapeutic effects of early and delayed window delivery of Gal-3C on cardiac function measured by echocardiography in terms of the ejection fraction, end systolic volume (ESV), and end diastolic volume (EDV). The ejection fraction is the fraction of blood ejected by the ventricle relative to its EDV. It is defined as the stroke volume (SV)/EDV×100. The SV is the EDV-ESV. Ejection fraction is most commonly measured using the non-invasive technique of echocardiography. Gal-3C administered for 7 days to animals beginning before ischemia-reperfusion injury (0-6 days post-MI; early window) or 4-10 days post-injury (delayed window) significantly benefited the ejection fraction and the ESV at d 28. However, there was no benefit from treatment on EDV at 28 days post-MI. There also was no benefit observed with the early window treatment at 2 days post-MI, which is before substantial remodeling has occurred. (Contrast with FIG. 9, which shows benefit in EDV at a later time.) Error bars=SD.
Figure 7:
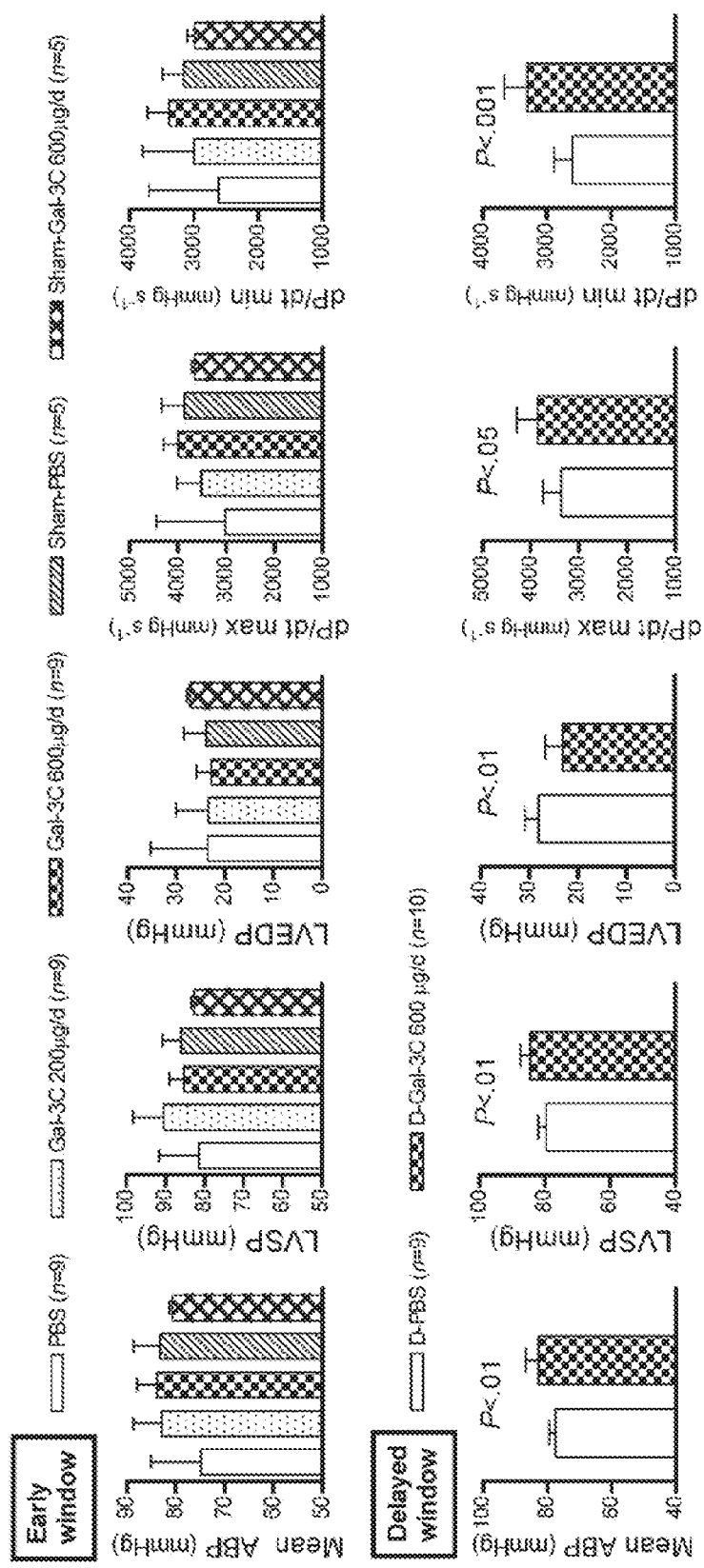
FIG. 7. Graphs of hemodynamic measurements indicate systolic and diastolic benefits of Gal-3C administration in the early and delayed delivery windows. Intraventricular pressure measurements of mean arterial blood pressure (ABP), LV systolic pressure (LVSP), LV end diastolic pressure (LVEDP), and dP/dt max and dP/dt min, which reflect contractility and relaxation kinetics, respectively, indicated significant improvements in all parameters for the delayed window, and was suggestive of improvements in most parameters for the early window that did not reach significance. Error bars=SD.

Animals receiving Gal-3C in the delayed window beginning 4 days post-MI experienced significant benefit in LV ejection fraction and ESV (FIG. 6, bottom panel), revealing beneficial effects on contractile function, as was the case for the early window. Also as observed with early window treatment, there was no benefit on LV EDV, as a measure of wall compliance, at 28 days post-MI. All of the five hemodynamic parameters were statistically significant improved by Gal-3C treatment in the delayed window (FIG. 7, bottom panel). It is concluded that administration during the delayed time window is as efficacious as administration early time window.

Figure 8B:
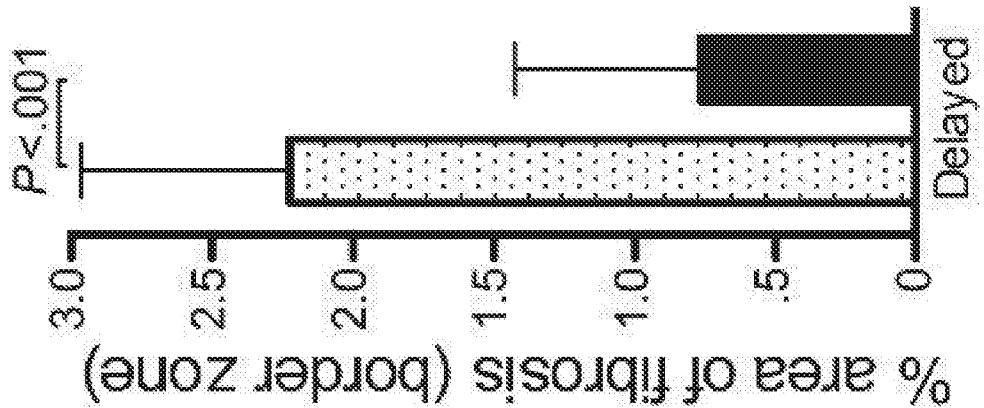
FIG. 8B. Interstitial (non-scar) fibrosis from the delayed window treatment group measured from quantitative analysis of Sirius Red-stained sections at or near the infarct border zone with the most scar from each heart as determined by the trichrome results. Delayed delivery (4-10 days post-MI) of Gal-3C substantially and significantly reduced the both infarct scar size and the border zone non-scar interstitial fibrosis. Error bars=SD.
Figure 8A:
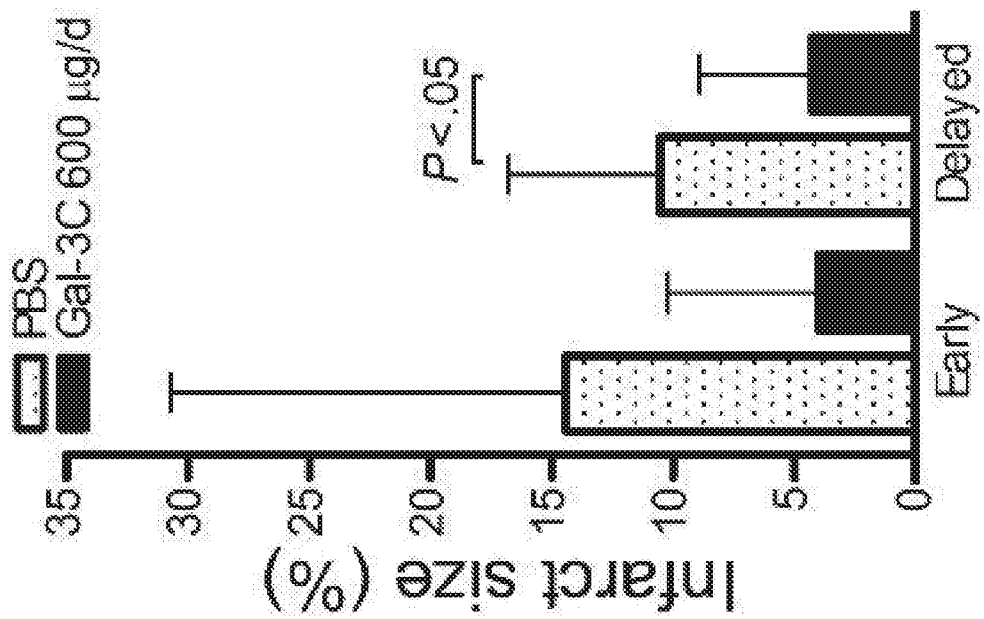
FIG. 8A. Infarct size measured from Masson's Trichrome-stained sections from the early and delayed window treatment groups.

After rats in the delayed treatment study were euthanized, hearts were harvested and sectioned for Masson's trichrome and Sirius red staining with quantitative image analysis to assess remodeling. Rather than using an optimized approach for infarct size measurement in permanent ligation rat models (64), it was confirmed that in the ischemia-reperfusion MI model, a volumetric infarct sizing approach (i.e., % area in the tissue sections that was scarred) would be more accurate. Using this approach for analysis of Masson's trichrome staining, it was shown that the infarct size was considerably (>2-fold) reduced in Gal-3C-treated (600 µg/day) rats, a difference that achieved significance with Gal-3C treatment in the delayed window (FIG. 8A). Furthermore, to determine if Gal-3C treatment also reduced interstitial (non-scar) fibrosis at and near the border zone of the infarct, quantitative analysis of Sirius red staining (FIG. 8B) for interstitial fibrosis was performed on tissue sections with the most scar from each heart as determined by the Masson's trichrome results. Interstitial fibrosis was dramatically reduced by ~65% in the rats receiving Gal-3C in the delayed window compared to the vehicle-only controls.

The levels of the inflammatory cytokines, IL-1β and IL-6, were determined in the plasma of sham control rats and rats with ischemia-reperfusion injury at 28 days post-injury (FIG. 5) using ELISA kits as described in Example 2 above. Controls implanted with pumps at 4 days post-MI containing vehicle-only (delayed PBS controls) expressed higher levels of IL-1β ((FIG. 5 left) compared to PBS controls in which implantation was prior to injury (PBS controls) showing that the timing of the pump implantation relative to the ischemia-reperfusion injury affected inflammatory potential. Also comparison of the injured PBS controls to the sham PBS controls revealed that ischemia-reperfusion injury induced IL-6 (FIG. 5 right), and that delayed window Gal-3C treatment did not have a significant effect on IL-6 levels, although early window Gal-3C treatment reduced plasma levels of IL-6. Importantly, the data indicate that treatment with Gal-3C at 600 µg/d beginning 4 days post-MI did not affect expression of either IL-1β or IL-6 at day 28 compared to animals implanted with pumps delivering vehicle-only on the same day (delayed PBS controls.)

Figure 9:
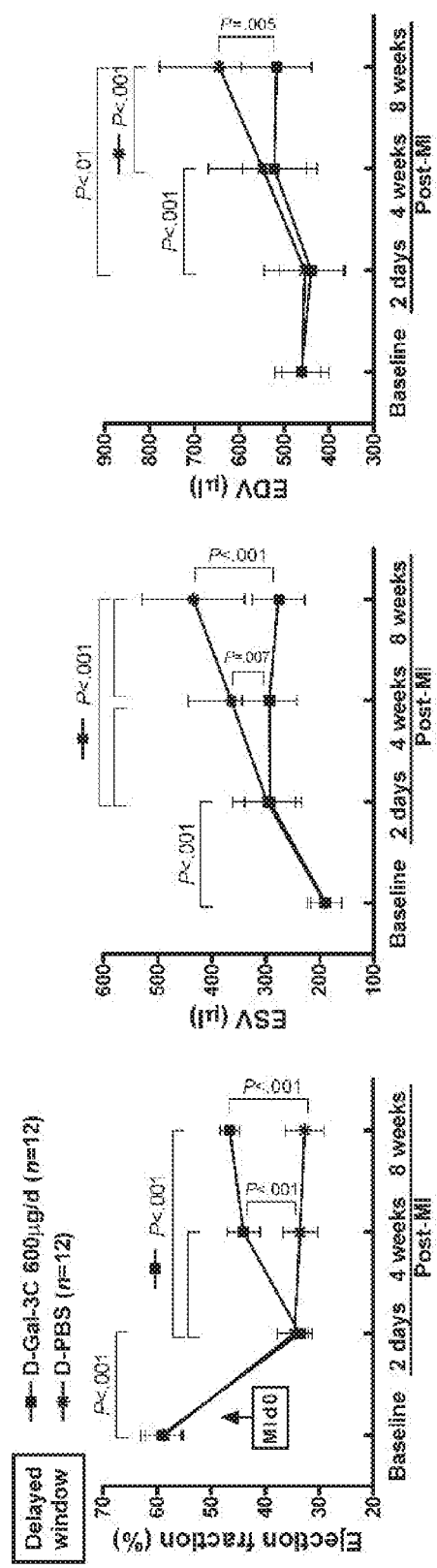
FIG. 9. Graphs showing the effects of delayed window delivery of Gal-3C on cardiac function measured by echocardiography out to 8 weeks post-MI. Gal-3C administered for 7 days from 4-10 days post-MI significantly benefited the ejection fraction and the ESV but not the EDV at 4 weeks (28 days post-MI) as in the prior results that were shown in FIG. 6. However, at 8 weeks (day 56) post-MI, echocardiography showed that there was beneficial effect on all three parameters including EDV from delayed window Gal-3C treatment. Continued decline in function in the PBS-only control group was shown by increased ESV and EDV at 8 weeks compared to 4 weeks. Error bars=SD.

Example 4: Long-Term Benefit from 7-Day Treatment of Rats with Gal-3C Beginning 4 Days Post Ischemic-Reperfusion Injury Improves Left Ventricular Diastolic Function In a subsequent experiment, high dose Gal-3C (600 µg/day) and vehicle-only were administered by Alzet pump over the delayed delivery window of 4-10 days post-MI to rats that had been subjected to the same ischemia-reperfusion procedure as described above in Example 2. However, in this experiment, serial echocardiography was performed at 2, 28, and 56 days (8 weeks) post-MI. The effect on cardiac function from Gal-3C treatment is shown in FIG. 9. The changes in ejection fraction, ESV, and EDV at 28 d post-MI were very similar to those obtained previously at 28 d post-MI as shown in FIG. 6 and described in Example 3. In the treated animals compared to the vehicle-only controls statistically significant improvements were observed in the ejection fraction and ESV but not in the EDV at 28 days (4 weeks) post-MI. However, at 8 weeks post-MI a significant benefit on EDV was detected in the Gal-3C treatment group. The significant decrease in the EDV in the Gal-3C treatment animals compared to the control animals at 8 weeks demonstrates the beneficial effect of Gal-3C treatment on wall compliance and diastolic function.

There also was a trend but not a statistically significant increase in the ejection fraction at 8 weeks compared to 4 weeks in the Gal-3C treated animals. The decrease in ESV was not of significantly greater magnitude after 8 weeks post-MI compared to that observed at 4 weeks post-MI. However, there were significant increases in the ESV and the EDV in the untreated controls at 8 compared to 4 weeks, results which showed that there was continuing benefit from the delayed treatment that prevented the declining functionality represented by the increase in ESV of the control animals over this period and indicating that Gal-3C treatment had a reparative effect on cardiac function.

Figure 10:
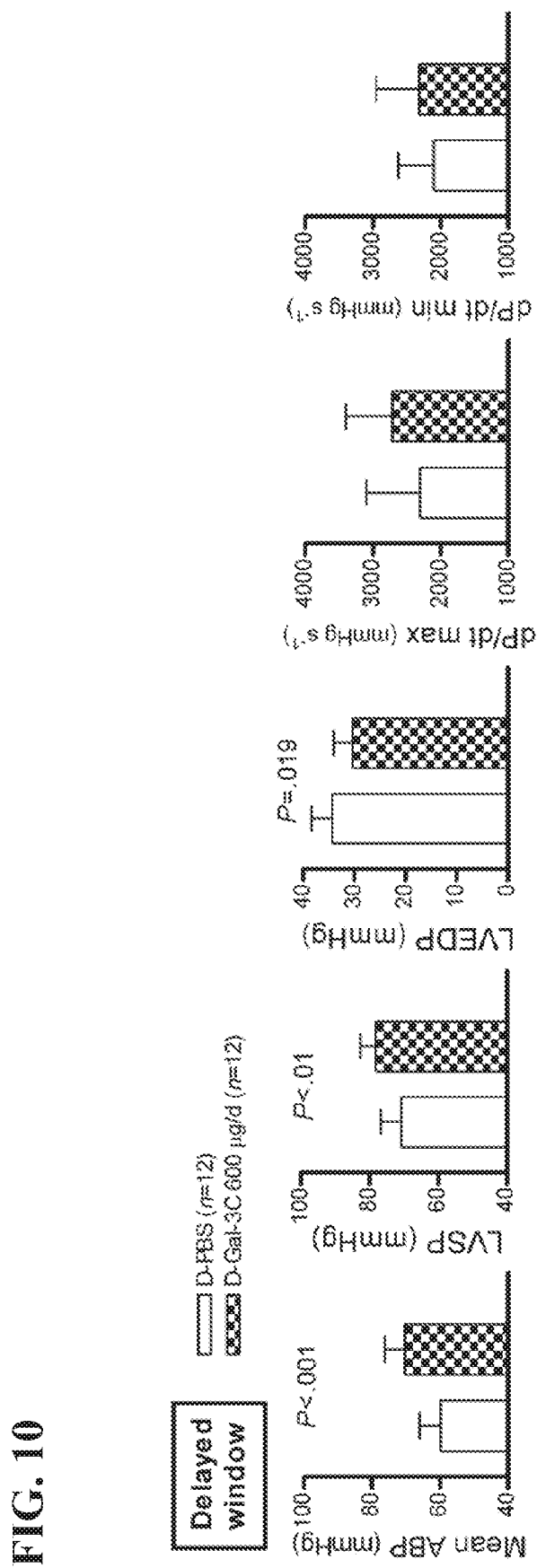
FIG. 10. Graphs of hemodynamic measurements indicates systolic and diastolic benefits of Gal-3C administration in the delayed delivery window. Intraventricular pressure measurements of mean ABP, LVSP, EDP, dP/dt max and dP/dt min are presented. The data indicated improvements in all parameters that were statistically significant for mean ABP, LVSP, and EDP, but only indicated trends for improvement in dP/dt max and dP/dt min that did not reach significance. Error bars=SD.

The hemodynamic parameters measured at the end of the 8 week follow-up period are presented in FIG. 10. Improvements were observed in Gal-3C treated animals compared to controls in all parameters that reached significance with the mean ABP, LVSP, and the LVEDP but not in dP/dt max and dP/dt min.

Figure 11B:
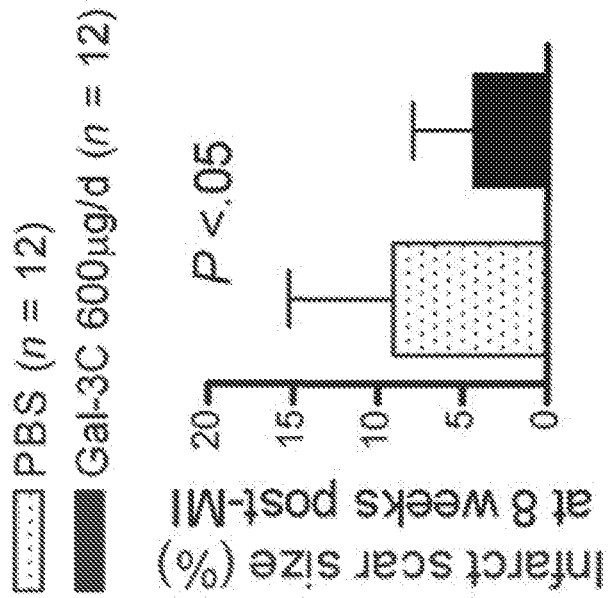
FIG. 11B. Interstitial (non-scar) fibrosis from the delayed window treatment group at 8 weeks post-MI and as measured from quantitative analysis of Sirius Red-stained sections at or near the infarct border zone with the most scar from each heart as determined by the trichrome results. Delayed delivery (days 4-10 post-MI) of Gal-3C substantially and significantly reduced the both infarct scar size and the border zone non-scar interstitial fibrosis. Error bars=SD FIG. 12. Graphs showing the effects of delayed window delivery of Gal-3C and of 56-day treatment with losartan on cardiac function measured by echocardiography out to 8 weeks post-MI. Gal-3C administered for 7 days from days 4-10 post-MI significantly benefited the ejection fraction and the ESV but not the EDV at 4 weeks (day 28) as in the prior results that were shown in FIG. 9. There was no significant benefit observed for losartan on the EF. At 8 weeks (day 56) post-MI, echocardiography showed that there was beneficial effect on all three parameters including EDV from delayed window Gal-3C treatment. Continued decline in function in the PBS-only control group was shown by increased ESV and EDV at 8 weeks compared to 4 weeks. Error bars=SD.
Figure 11A:
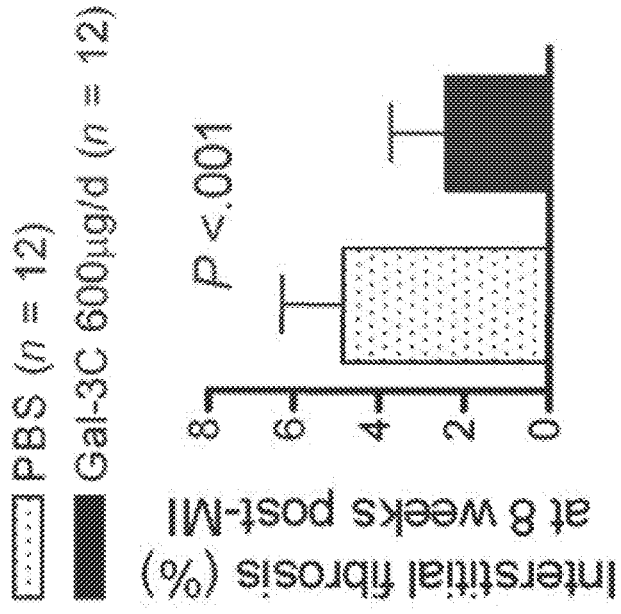
FIG. 11A. Infarct size measured from Masson's Trichrome-stained sections at 8 weeks post-MI from the delayed window treatment groups.

As described in Example 3 above, rats were euthanized at 8 weeks post-MI, hearts were harvested and sectioned for Masson's trichrome and Sirius red staining with quantitative image analysis using a volumetric infarct sizing approach (i.e., % area in the tissue sections that was scarred) for analysis of Masson's trichrome staining to calculate the size of the primary infarct. Using this approach, it was revealed that infarct size was significantly smaller in the Gal-3C group than the PBS group at 8 weeks post-MI (FIG. 11A).

Quantitative histology of Sirius red staining for interstitial fibrosis was performed on tissue sections with the most scar from each heart as described above in Example 3 using ImageJ. This analysis revealed that there was a reduction of interstitial fibrosis by roughly 50% in Gal-3C treated animals relative to vehicle-only controls (n=12/group; Gal-3C: 2.4+/−1.3% SD versus PBS-only control: 4.8+/−1.4% SD; P=0.0003 by two-tailed t-test) at 8 weeks post-MI (FIG. 11B).

The results presented herein indicate that overall Gal-3C acts not on the early inflammatory period of the response to MI but in the late period to improve repair processes that lead to ECM deposition, infarct scar formation, and remote fibrosis. The improvements observed by delayed treatment with Gal-3C that increased the ejection fraction at 4 and 8 weeks post-MI compared to the ejection fraction at 2 days post-MI suggest that this protein not only may have capability to prevent remodeling post-MI but also may have ability to reverse remodeling and fibrosis.

Example 5: Inhibition of Cardiac Fibrosis Using Homologs of the N-Terminally Truncated Galectin-3

Specific examples of modifications of the Gal-3C sequence include conserved mutation substitutions of one or more amino acids occurring between position 201 and 230. Possible conserved mutation substitutions include the following, where the amino acid on the left is the original and the amino acid on the right is the substituted amino acid.

| | | |
|---|---|---|
| Val-202 | → | Ala |
| Val-204 | → | Ala |
| Glu-205 | → | Asp |
| Asp-207 | → | Glu |
| His-208 | → | Arg |
| Phe-209 | → | Leu |
| Val-211 | → | Ala |
| Ala-212 | → | Val |
| Asp-215 | → | Glu |
| Ala-216 | → | Val |
| His-217 | → | Arg |
| Tyr-221 | → | Phe |
| His-223 | → | Arg |
| Val-225 | → | Ala |
| Glu-230 | → | Asp |

Amino acid substitutions are performed using a PCR-based site-directed mutagenesis kit. To make the substitution of Asp-207→Glu, the oligonucleotide primer used is the following sequence.

```
                                        (SEQ ID NO: 9)
5' GTT GAA CCT GAA CAC TTC AAG GTT 3'
```

A plasmid containing the Δ107 galectin-3 coding sequence in a pET32 expression system can be used as a template in a PCR reaction using primers designed to amplify the desired fragment.

```
Forward primer:
                                       (SEQ ID NO: 10)
5' GACGACGACAAGGGCGCCCCTGCTGGG 3'

Reverse primer:
                                       (SEQ ID NO: 11)
5' GAGGAGAAGCCCGGTTTATATCATGGTATA 3'
```

Underlined sequences in each of the primers match the plasmid sequences for pET32 (EK/LIC expression system, Novagen, Madison, Wis.). The reverse primer defines the C-terminal protein sequence and does not differ in these procedures. The non-underlined portion of the forward primer defines the N-truncated version of the native galectin-3 that in this example begins with Gly-108 (Δ1-107″, starting at amino acid sequence glycine, alanine, proline, alanine, etc.). The underlined sequences are added as tails and are used to fuse the PCR product with the pET32 Ek/LIC plasmid using the Ek/LIC ligation protocol (Novagen, Madison, Wis.). This particular plasmid produces a fusion protein with a variety of unique binding qualities and endoprotease sites allowing for high yields and purity of the recombinant protein. More than one cysteine can be introduced to the construct by simply including more cysteine codons (either tgt or tgc) to create a version of N-truncated galectin-3 having one or more cysteines where they should not interfere with carbohydrate binding, for example, at the N- or C-terminus.

*E. coli* BL21(DE3) bacteria are transformed with the above-described construct and the bacteria can be used for protein production. Expression is under the control of bacteriophage T7 transcription and can be induced by providing a source of T7 RNA polymerase, such as infection with a phage that carries the T7 RNA polymerase gene or moving the plasmid into a cell containing an expression host containing a copy of the T7 RNA polymerase gene.

This construct can be produced by other cloning methods as well and the amino acid sequence is designated as SEQ ID NO: 7, and is as follows:

```
                                            (SEQ ID NO: 7)
GAP AGPLIVPYNL PLPGGVVPRM LITILGTVKP NANRIALDFQ

RGNDVAFHFN PRFNENNRRV IVCNTKLDNN WGREERQSVF

PFESGKPFKI QVLVEPEHFK VAVNDAHLLQ YNHRVKKLNE

ISKLGISGDI DLTSASYTMI.
```

To make the substitution of Val-225→Ala the oligonucleotide primer used is the following sequence.

```
                                       (SEQ ID NO: 12)
5' AAT CAT CGG GCT AAA AAA CTC AAT 3'
```

This construct can be produced by other cloning methods as well and the amino acid sequence is designated as SEQ ID NO: 8, and is as follows:

```
                                            (SEQ ID NO: 8)
GAP AGPLIVPYNL PLPGGVVPRM LITILGTVKP NANRIALDFQ

RGNDVAFHFN PRFNENNRRV IVCNTKLDNN WGREERQSVF

PFESGKPFKI QVLVEPEHFK VAVNDAHLLQ YNHRAKKLNE

ISKLGISGDI DLTSASYTMI
```

In vitro site-directed mutagenesis is a technique that can be used for carrying out a substitution at one or several sites specifically. Stratagene's (La Jolla, Calif.) QuikChange® XL site-directed mutagenesis kit (U.S. Pat. Nos. 5,789,166; 5,923,419; 6,391,548 and patents pending) allows site-specific mutation in virtually any double-stranded plasmid, thus eliminating the need for subcloning into M13-based bacteriophage vectors and for single-stranded DNA rescue. The QuikChange XL system is used to make point mutations, switch amino acids, and delete or insert single or multiple amino acids. The QuikChange XL system requires no specialized vectors, unique restriction sites, or multiple transformations. This four-step procedure generates mutants with greater than 80% efficiency. The protocol uses either miniprep plasmid DNA or cesium-chloride-purified DNA. Stratagene's QuikChange Multi System enables mutagenesis at multiple sites in a single round, using a single oligonucleotide per site. It also makes it easy to randomize key amino acids using oligos containing degenerate codons. A rapid three-step procedure introduces mutations at three different sites simultaneously in the 4-kb QuikChange Multi control plasmid with greater than 50% efficiency.

The QuikChange XL method is performed using Pfu-Turbo® DNA polymerase and a thermal temperature cycler. PfuTurbo DNA polymerase replicates both plasmid strands without displacing the mutant oligonucleotide primers. The basic procedure utilizes a supercoiled double stranded DNA (dsDNA) vector with an insert of interest and two synthetic oligonucleotide primers containing the desired mutation. The oligonucleotide primers, each complementary to opposite strands of the vector, are extended during temperature cycling by using PfuTurbo DNA polymerase. Incorporation of the oligonucleotide primers generates a mutated plasmid containing staggered nicks. Following temperature cycling, the product is treated with Dpn I. The Dpn I endonuclease (target sequence: 5'-Gm6ATC-3') is specific for methylated and hemimethylated DNA and is used to digest the parental DNA template and to select for mutation containing synthesized DNA. DNA isolated from almost all *E. coli* strains is dam methylated and therefore susceptible to Dpn I digestion. The nicked vector DNA incorporating the desired mutations is then transformed into XL10-Gold® ultracompetent cells. The small amount of starting DNA template required to perform this method, the high fidelity of the PfuTurbo DNA polymerase, and the low number of thermal cycles all contribute to the high mutation.

Example 6: Conversion of Dosing of Gal-3C from One Species to Another

As provided herein, to convert doses from one species to another, the surface area normalization method can be used. Extrapolation of an animal dose to a human dose can be done in one step using the appropriate body surface area conversion factor (BSA-CF) that is a unitless number that converts milligram per kilogram doses for each animal species to the mg/kg dose in humans (69). The value of the BSA-CF for rats to humans is 6.2. As provided herein, to convert a daily dose of Gal-3C in rats, as in Example 3, of 600 μg/day per 300 gram rat, the value of 2 milligrams per kilogram is divided by 6.2 that is equal to 0.32 milligrams per kilogram. Using this method, then, the human equivalent dose for a 60 kilogram (132 pound) person is 19.2 milligrams per day (0.32 milligrams per kilogram×60 kilograms), and for a 90 kilogram person (200 pounds) is 28.8 milligrams per day.

A human equivalent of the daily dose of 1.2 micrograms per gram in the mouse (=1.2 milligram per kilogram) is approximately 0.1 milligrams per kilogram since the BSA-CF for mice is 12.3.

Example 7: Greater Long-Term Benefit from 7-Day Treatment of Rats with Gal-3C Beginning 4 Days Post Ischemic-Reperfusion Injury Compared to 56-Day Treatment with Losartan Beginning on the Day of Injury To expand upon the previous experiments described in Example 4, thereby enabling comparison with a currently used post-MI therapy, an additional group was added that received the vehicle by Alzet pump over the delayed delivery window of 4-10 d post-MI as before. In order to enable blind comparison to the Gal-3C and vehicle control groups already analyzed, the group size was increased to 15/group with 3 rats added for treatment with high dose Gal-3C (600 μg/day) and 3 rats added for treatment with vehicle alone wherein both treatments were administered by Alzet pump. Thus, the new losartan treatment group was added to the experiment but the investigator was blinded as to whether a given rat was from the new losartan group or the newly expanded Gal-3C and vehicle-only groups. All animals were subjected to the same ischemia/reperfusion procedure as described above in Example 2. A group of 15 of the vehicle-only animals were also treated with the angiotensin receptor blocker (ARB) losartan (8 mg/kg/day) in the drinking water beginning immediately after MI and continuing over the 56-day experiment as previously described (58).

Figure 12:
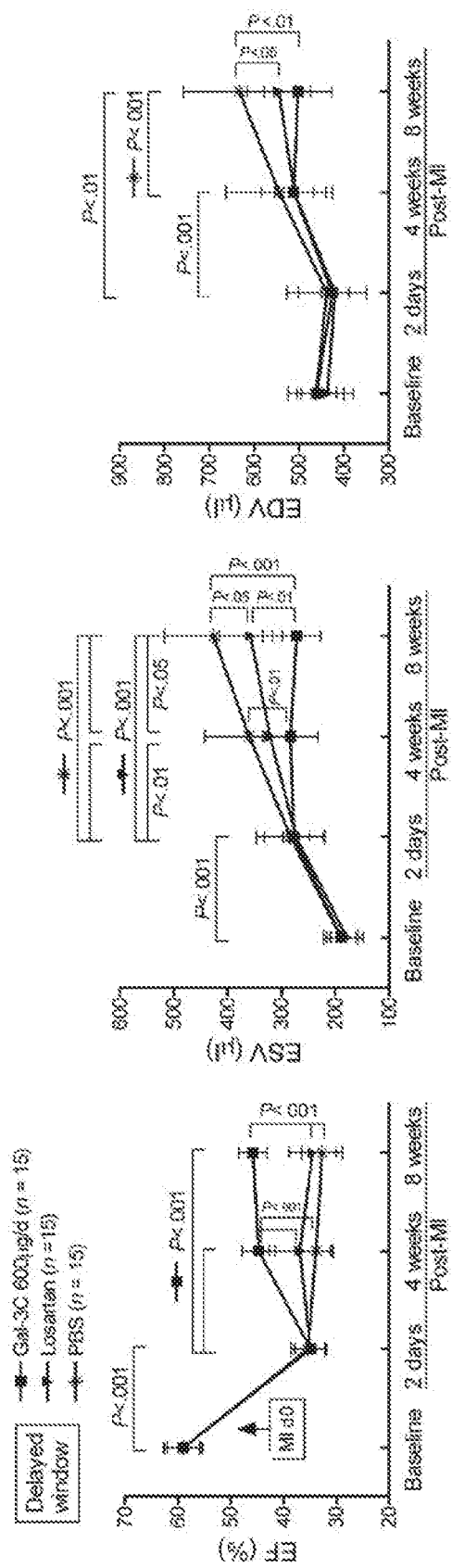
Figure 13:
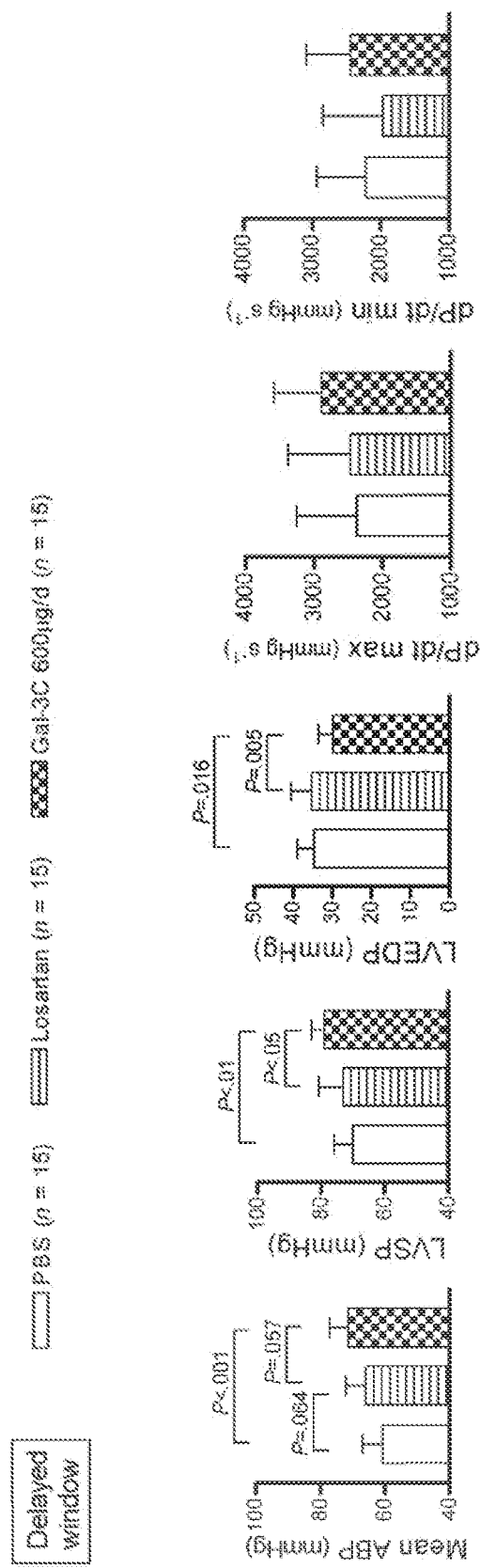
FIG. 13. Graphs of hemodynamic measurements indicate systolic and diastolic benefits of Gal-3C administration in the delayed delivery window and of 56-day treatment with losartan. Intraventricular pressure measurements of mean ABP, LVSP, LVEDP, dP/dt max and dP/dt min are presented. The data indicated improvements in all parameters that were statistically significant for mean ABP, LVSP, and LVEDP, but only indicated trends for improvement in dP/dt max and dP/dt min that did not reach significance from Gal-3C administration. There was no significant benefit from losartan treatment on the mean ABP, LVSP, or LVEDP. Error bars=SD.

Serial echocardiography was performed at 2, 28, and 56 days (8 weeks) post-MI and terminal intraventricular pressure catheter measurements were obtained. The effect on cardiac function from losartan was compared to the effect of Gal-3C that included data from the 12 animals in the Gal-3C and the 12 animals in the vehicle-only group that were presented in FIG. 9 and FIG. 10. The results (FIG. 12 and FIG. 13) showed that there was statistically significant benefit from Gal-3C relative to PBS where no significant benefit was observed for losartan on the EF, mean ABP, LVSP, and LVEDP. Furthermore, there were three parameters in which GAL-3C treatment produced a statistically significant benefit relative to losartan: ESV, LVSP, and LVEDP. In patients with heart failure with reduced EF, long-term therapy with an ARB has been found to reduce the risk of death. The results described herein indicate that treatment with Gal-3C post-MI would be more beneficial on recovery and preservation of heart function compared to treatment with losartan or another ARB alone.

REFERENCES

1. Frangogiannis, N. G. 2008. The immune system and cardiac repair. Pharmacol Res. 58:88-111.
2. Henderson, N. C., and Sethi, T. 2009. The regulation of inflammation by galectin-3. Immunol Rev. 230:160-171.
3. Jugdutt, B. I. (2013) Regulation of Fibrosis After MI: Implications for Ventricular Remodeling. in *Cardiac Remodeling—Molecular Mechanisms* (Judgutt, B. I., and Naranjan, S. D. eds.), Springer, New York. pp 525-557
4. Jugdutt, B. I. 2009. Limiting fibrosis after MI. N Engl J Med. 360:1567-1569.
5. Jugdutt, B. I. 2008. Aging and remodeling during healing of the wounded heart: current therapies and novel drug targets. Curr Drug Targets. 9:325-344.
6. Frangogiannis, N. G. 2012. Regulation of the inflammatory response in cardiac repair. Circ Res. 110:159-173.
7. Frangogiannis, N. G., Smith, C. W., and Entman, M. L. 2002. The inflammatory response in MI. Cardiovasc Res. 53:31-47.
8. Jugdutt, B. I. 2003. Ventricular remodeling after infarction and the extracellular collagen matrix: when is enough enough? Circulation. 108:1395-1403.
9. Grossman, W. 2000. Defining diastolic dysfunction. Circulation. 101:2020-2021.
10. Borthwick, L. A., Wynn, T. A., and Fisher, A. J. 2013. Cytokine mediated tissue fibrosis. Biochim Biophys Acta. 1832:1049-1060.
11. Barondes, S. H., Castronovo, V., Cooper, D. N., Cummings, R. D., Drickamer, K., Feizi, T., Gitt, M. A., Hirabayashi, J., Hughes, C., Kasai, K., and et al. 1994. Galectins: a family of animal beta-galactoside-binding lectins [letter]. Cell. 76:597-598.
12. Liu, F. T., and Rabinovich, G. A. 2005. Galectins as modulators of tumour progression. Nat Rev Cancer. 5:29-41. 15366962 NLM MEDLINE.

13. Hsu, D. K., Zuberi, R. I., and Liu, F. T. 1992. Biochemical and biophysical characterization of human recombinant IgE-binding protein, an S-type animal lectin. J. Biol. Chem. 267:14167-14174.
14. Hirabayashi, J., Hashidate, T., Arata, Y., Nishi, N., Nakamura, T., Hirashima, M., Urashima, T., Oka, T., Futai, M., Muller, W., Yagi, F., and Kasai, K. 2002. Oligosaccharide specificity of galectins: a search by frontal affinity chromatography. Biochim Biophys Acta. 1572:232-254.
15. Inohara, H., and Raz, A. 1995. Functional evidence that cell surface galectin-3 mediates homotypic cell adhesion. Cancer Res. 55:3267-3271.
16. Nieminen, J., Kuno, A., Hirabayashi, J., and Sato, S. 2007. Visualization of galectin-3 oligomerization on the surface of neutrophils and endothelial cells using fluorescence resonance energy transfer. J Biol Chem. 282:1374-1383.
17. Massa, S. M., Cooper, D. N., Leffler, H., and Barondes, S. H. 1993. L-29, an endogenous lectin, binds to glycoconjugate ligands with positive cooperativity. Biochemistry. 32:260-267.
18. Ahmad, N., Gabius, H. J., Andre, S., Kaltner, H., Sabesan, S., Roy, R., Liu, B., Macaluso, F., and Brewer, C. F. 2004. Galectin-3 precipitates as a pentamer with synthetic multivalent carbohydrates and forms heterogeneous cross-linked complexes. J Biol Chem. 279:10841-10847.
19. Partridge, E. A., Le Roy, C., Le Roy, C., Di Guglielmo, G. M., Di Guglielmo, G. M., Pawling, J., Pawling, J., Cheung, P., Cheung, P., Granovsky, M., Granovsky, M., Nabi, I. R., Nabi, I. R., Wrana, J. L., Wrana, J. L., Dennis, J. W., and Dennis, J. W. 2004. Regulation of cytokine receptors by Golgi N-glycan processing and endocytosis. Science. 306:120-124. 15735118 NLM MEDLINE.
20. Hughes, R. C. 1999. Secretion of the galectin family of mammalian carbohydrate-binding proteins. Biochim Biophys Acta. 1473:172-185.
21. Menon, R. P., and Hughes, R. C. 1999. Determinants in the N-terminal domains of galectin-3 for secretion by a novel pathway circumventing the endoplasmic reticulum-Golgi complex. Eur J Biochem. 264:569-576.
22. Mehul, B., and Hughes, R. C. 1997. Plasma membrane targetting, vesicular budding and release of galectin 3 from the cytoplasm of mammalian cells during secretion. J Cell Sci. 110:1169-1178.
23. Sato, S., and Hughes, R. C. 1994. Regulation of secretion and surface expression of Mac-2, a galactoside-binding protein of macrophages. J Biol Chem. 269:4424-4430.
24. Gaudin, J. C., Mehul, B., and Hughes, R. C. 2000. Nuclear localisation of wild type and mutant galectin-3 in transfected cells. Biol Cell. 92:49-58.
25. Davidson, P. J., Davis, M. J., Patterson, R. J., Ripoche, M. A., Poirier, F., and Wang, J. L. 2002. Shuttling of galectin-3 between the nucleus and cytoplasm. Glycobiology. 12:329-337.
26. Haudek, K. C., Spronk, K. J., Voss, P. G., Patterson, R. J., Wang, J. L., and Arnoys, E. J. 2009. Dynamics of galectin-3 in the nucleus and cytoplasm. Biochim Biophys Acta. 1800:181-189.
27. van den Brule, F. A., Waltregny, D., Liu, F. T., and Castronovo, V. 2000. Alteration of the cytoplasmic/nuclear expression pattern of galectin-3 correlates with prostate carcinoma progression. Int J Cancer. 89:361-367.

28. Openo, K. P., Kadrofske, M. M., Patterson, R. J., and Wang, J. L. 2000. Galectin-3 expression and subcellular localization in senescent human fibroblasts. Exp Cell Res. 255:278-290.
29. Davidson, P. J., Li, S. Y., Lohse, A. G., Vandergaast, R., Verde, E., Pearson, A., Patterson, R. J., Wang, J. L., and Arnoys, E. J. 2006. Transport of galectin-3 between the nucleus and cytoplasm. I. Conditions and signals for nuclear import. Glycobiology. 16:602-611.
30. Li, S. Y., Davidson, P. J., Lin, N. Y., Patterson, R. J., Wang, J. L., and Arnoys, E. J. 2006. Transport of galectin-3 between the nucleus and cytoplasm. II. Identification of the signal for nuclear export. Glycobiology. 16:612-622.
31. Nakahara, S., Oka, N., Wang, Y., Hogan, V., Inohara, H., and Raz, A. 2006. Characterization of the nuclear import pathways of galectin-3. Cancer Res. 66:9995-10006.
32. Sharma, U. C., Pokharel, S., van Brakel, T. J., van Berlo, J. H., Cleutjens, J. P., Schroen, B., Andre, S., Crijns, H. J., Gabius, H. J., Maessen, J., and Pinto, Y. M. 2004. Galectin-3 marks activated macrophages in failure-prone hypertrophied hearts and contributes to cardiac dysfunction. Circulation. 110:3121-3128.
33. Inohara, H., Akahani, S., and Raz, A. 1998. Galectin-3 stimulates cell proliferation. Exp Cell Res. 245:294-302.
34. Jia, W., Kidoya, H., Yamakawa, D., Naito, H., and Takakura, N. 2013. Galectin-3 accelerates M2 macrophage infiltration and angiogenesis in tumors. Am J Pathol. 182:1821-1831.
35. McCullough, P. A., Olobatoke, A., and Vanhecke, T. E. 2011. Galectin-3: a novel blood test for the evaluation and management of patients with heart failure. Rev Cardiovasc Med. 12:200-210.
36. Lok, D. J., Van Der Meer, P., de la Porte, P. W., Lipsic, E., Van Wijngaarden, J., Hillege, H. L., and van Veldhuisen, D. J. 2011. Prognostic value of galectin-3, a novel marker of fibrosis, in patients with chronic heart failure: data from the DEAL-HF study. Clin Res Cardiol. 99:323-328.
37. de Boer, R. A., van Veldhuisen, D. J., Gansevoort, R. T., Muller Kobold, A. C., van Gilst, W. H., Hillege, H. L., Bakker, S. J., and van der Harst, P. 2011. The fibrosis marker galectin-3 and outcome in the general population. J Intern Med. 272:55-64.
38. Meijers, W. C., van der Velde, A. R., and de Boer, R. A. 2014. The ARCHITECT galectin-3 assay: comparison with other automated and manual assays for the measurement of circulating galectin-3 levels in heart failure. Expert Rev Mol Diagn. 14:257-266.
39. de Boer, R. A., van der Velde, A. R., Mueller, C., van Veldhuisen, D. J., Anker, S. D., Peacock, W. F., Adams, K. F., and Maisel, A. 2014. Galectin-3: a modifiable risk factor in heart failure. Cardiovasc Drugs Ther. 28:237-246.
40. Jarvis, G. A., John, C. M., and Leffler, H. 2001. N-terminally truncated galectin-3 for use in treating cancer. U.S. Pat. No. 6,770,622. 6,770,622
41. John, C. M., Leffler, H., Kahl-Knutsson, B., Svensson, I., and Jarvis, G. A. 2003. Truncated galectin-3 inhibits tumor growth and metastasis in orthotopic nude mouse model of human breast cancer. Clin Cancer Res. 9:2374-2383.
42. Liu, F. T., Hsu, D. K., Zuberi, R. I., Kuwabara, I., Chi, E. Y., and Henderson, W. R., Jr. 1995. Expression and function of galectin-3, a beta-galactoside-binding lectin, in human monocytes and macrophages. Am J Pathol. 147:1016-1028.

43. Liu, F. T., Hsu, D. K., Zuberi, R. I., Hill, P. N., Shenhav, A., Kuwabara, I., and Chen, S. S. 1996. Modulation of functional properties of galectin-3 by monoclonal antibodies binding to the non-lectin domains. Biochemistry. 35:6073-6079.
44. Ochieng, J., Green, B., Evans, S., James, O., and Warfield, P. 1998. Modulation of the biological functions of galectin-3 by matrix metalloproteinases. Biochim Biophys Acta. 1379:97-106.
45. Balan, V., Nangia-Makker, P., Jung, Y. S., Wang, Y., and Raz, A. 2010. Galectin-3: A novel substrate for c-Abl kinase. Biochim Biophys Acta. 1803:1198-1205.
46. Balan, V., Nangia-Makker, P., Kho, D. H., Wang, Y., and Raz, A. 2012. Tyrosine-phosphorylated galectin-3 protein is resistant to prostate-specific antigen (PSA) cleavage. J Biol Chem. 287:5192-5198.
47. Markowska, A. I., Liu, F. T., and Panjwani, N. 2010. Galectin-3 is an important mediator of VEGF- and bFGF-mediated angiogenic response. J Exp Med. 207:1981-1993.
48. Jarvis, G. A., Mirandola, L., Cobos, E., Chiriva-Internati, M., and John, C. M. (2012) Galectin-3C: human lectin for treatment of cancer. in *Galectins and Disease Implications for Targeted Therapeutics* (Klyosov, A. A., and Traber, P. G. eds.), American Chemical Society. pp 195-232
49. Oda, Y., Leffler, H., Sakakura, Y., Kasai, K., and Barondes, S. H. 1991. Human breast carcinoma cDNA encoding a galactoside-binding lectin homologous to mouse Mac-2 antigen. Gene. 99:279-283.
50. Elena, C., Ravasi, P., *Castelli*, M. E., Peiru, S., and Menzella, H. G. 2014. Expression of codon optimized genes in microbial systems: current industrial applications and perspectives. Front Microbiol. 5:21.
51. Seetharaman, J., Kanigsberg, A., Slaaby, R., Leffler, H., Barondes, S. H., and Rini, J. M. 1998. X-ray crystal structure of the human galectin-3 carbohydrate recognition domain at 2.1-A resolution. J Biol Chem. 273:13047-13052.
52. Smith, G. P. 1991. Surface presentation of protein epitopes using bacteriophage expression systems. Curr Opin Biotechnol. 2:668-673.
53. Clackson, T., and Wells, J. A. 1994. In vitro selection from protein and peptide libraries. Trends Biotechnol. 12:173-184.
54. National Heart, L., and Blood Institute. 2008. NHLBI Financial Year 2008 Fact Book.
55. Nahrendorf, M., Pittet, M. J., and Swirski, F. K. 2010. Monocytes: protagonists of infarct inflammation and repair after MI. Circulation. 121:2437-2445.
56. Page, R. L., 2nd, Ghushchyan, V., and Nair, K. 2011. A call to action: responding to the future forecasting of cardiovascular disease in America. Am Health Drug Benefits. 4:280-288.
57. Heidenreich, P. A., Trogdon, J. G., Khavjou, O. A., Butler, J., Dracup, K., Ezekowitz, M. D., Finkelstein, E. A., Hong, Y., Johnston, S. C., Khera, A., Lloyd-Jones, D. M., Nelson, S. A., Nichol, G., Orenstein, D., Wilson, P. W., Woo, Y. J., American Heart Association Advocacy Coordinating, C., Stroke, C., Council on Cardiovascular, R., Intervention, Council on Clinical, C., Council on, E., Prevention, Council on, A., Thrombosis, Vascular, B., Council on, C., Critical, C., Perioperative, Resuscitation, Council on Cardiovascular, N., Council on the Kidney in Cardiovascular, D., Council on Cardiovascular, S., Anesthesia, Interdisciplinary Council on Quality of, C., and Outcomes, R. 2011. Forecasting the future of cardiovascular disease in the United States: a policy statement from the American Heart Association. Circulation. 123:933-944.
58. Silvestre, J. S., Heymes, C., Oubenaissa, A., Robert, V., Aupetit-Faisant, B., Carayon, A., Swynghedauw, B., and Delcayre, C. 1999. Activation of cardiac aldosterone production in rat MI: effect of angiotensin II receptor blockade and role in cardiac fibrosis. Circulation. 99:2694-2701.
59. Mill, J. G., Milanez Mda, C., de Resende, M. M., Gomes Mda, G., and Leite, C. M. 2003. Spironolactone prevents cardiac collagen proliferation after MI in rats. Clin Exp Pharmacol Physiol. 30:739-744.
60. Santiago, J. J., Dangerfield, A. L., Rattan, S. G., Bathe, K. L., Cunnington, R. H., Raizman, J. E., Bedosky, K. M., Freed, D. H., Kardami, E., and Dixon, I. M. 2010. Cardiac fibroblast to myofibroblast differentiation in vivo and in vitro: expression of focal adhesion components in neonatal and adult rat ventricular myofibroblasts. Dev Dyn. 239:1573-1584.
61. Springer, M. L., Sievers, R. E., Viswanathan, M. N., Yee, M. S., Foster, E., Grossman, W., and Yeghiazarians, Y. 2005. Closed-chest cell injections into mouse myocardium guided by high-resolution echocardiography. Am J Physiol Heart Circ Physiol. 289:H1307-1314.
62. Zhang, Y., Sievers, R. E., Prasad, M., Mirsky, R., Shih, H., Wong, M. L., Angeli, F. S., Ye, J., Takagawa, J., Koskenvuo, J. W., Springer, M. L., Grossman, W., Boyle, A. J., and Yeghiazarians, Y. 2011. Timing of bone marrow cell therapy is more important than repeated injections after MI. Cardiovasc Pathol. 20:204-212.
63. Yeghiazarians, Y., Zhang, Y., Prasad, M., Shih, H., Saini, S. A., Takagawa, J., Sievers, R. E., Wong, M. L., Kapasi, N. K., Mirsky, R., Koskenvuo, J., Minasi, P., Ye, J., Viswanathan, M. N., Angeli, F. S., Boyle, A. J., Springer, M. L., and Grossman, W. 2009. Injection of bone marrow cell extract into infarcted hearts results in functional improvement comparable to intact cell therapy. Mol Ther. 17:1250-1256. PMC2835212.
64. Takagawa, J., Zhang, Y., Wong, M. L., Sievers, R. E., Kapasi, N. K., Wang, Y., Yeghiazarians, Y., Lee, R. J., Grossman, W., and Springer, M. L. 2007. Myocardial infarct size measurement in the mouse chronic infarction model: comparison of area- and length-based approaches. J Appl Physiol. 102:2104-2111. PMC2675697.
65. Wang, X., Takagawa, J., Haddad, D. J., Pinnamaneni, K., Zhang, Y., Sievers, R. E., Grossman, W., Yeghiazarians, Y., and Springer, M. L. 2011. Advanced Donor Age Impairs Bone Marrow Cell Therapeutic Efficacy for Cardiac Disease. J Tissue Sci Eng. S3:002. PMC3366554.
66. Wang, X., Takagawa, J., Lam, V. C., Haddad, D. J., Tobler, D. L., Mok, P. Y., Zhang, Y., Clifford, B. T., Pinnamaneni, K., Saini, S. A., Su, R., Bartel, M. J., Sievers, R. E., Carbone, L., Kogan, S., Yeghiazarians, Y., Hermiston, M., and Springer, M. L. 2011. Donor MI impairs the therapeutic potential of bone marrow cells by an interleukin-1-mediated inflammatory response. Sci Transl Med. 3:100ra90. PMC3350804.
67. Mihardja, S. S., Gao, D., Sievers, R. E., Fang, Q., Feng, J., Wang, J., Vanbrocklin, H. F., Larrick, J. W., Huang, M., Dae, M., and Lee, R. J. 2010. Targeted in vivo extracellular matrix formation promotes neovascularization in a rodent model of MI. PLoS One. 5:e10384.
68. Patten, R. D., and Hall-Porter, M. R. 2009. Small animal models of heart failure: development of novel therapies, past and present. Circ Heart Fail. 2:138-144.

69. F.D.A. 2005. Guidance for Industry: Estimating the Maximum Safe Starting Dose in Initial Clinical Trials for Therapeutics in Adult Healthy Volunteers. (Research, C. f D. E. a. ed., Rockville, Md.

70. Mirandola, L., Yu, Y., Chui, K., Jenkins, M. R., Cobos, E., John, C. M., and Chiriva-Internati, M. 2011. Galectin-3C Inhibits Tumor Growth and Increases the Anticancer Activity of Bortezomib in a Murine Model of Human Multiple Myeloma. PLoS One. 6:e21811; PMC3135605.

71. Choi, S. S., Sicklick, J. K., Ma, Q., Yang, L., Huang, J., Qi, Y., Chen, W., Li, Y. X., Goldschmidt-Clermont, P. J., and Diehl, A. M. 2006. Sustained activation of Rac1 in hepatic stellate cells promotes liver injury and fibrosis in mice. Hepatology. 44:1267-1277.

72. Cui, W., Matsuno, K., Iwata, K., Ibi, M., Matsumoto, M., Zhang, J., Zhu, K., Katsuyama, M., Torok, N. J., and Yabe-Nishimura, C. 2011. NOX1/nicotinamide adenine dinucleotide phosphate, reduced form (NADPH) oxidase promotes proliferation of stellate cells and aggravates liver fibrosis induced by bile duct ligation. Hepatology. 54:949-958.

73. Nguyen, D. T., Ding, C., Wilson, E., Marcus, G. M., and Olgin, J. E. 2010. Pirfenidone mitigates left ventricular fibrosis and dysfunction after MI and reduces arrhythmias. Heart Rhythm. 7:1438-1445.

74. Granovsky, M., Fata, J., Pawling, J., Muller, W. J., Khokha, R., and Dennis, J. W. 2000. Suppression of tumor growth and metastasis in Mgat5-deficient mice. Nat Med. 6:306-312.

75. Dennis, J. W., Pawling, J., Cheung, P., Partridge, E., and Demetriou, M. 2002. UDP-N-acetylglucosamine:alpha-6-D-mannoside beta1,6 N-acetylglucosaminyltransferase V (Mgat5) deficient mice. Biochim Biophys Acta. 1573: 414-422.

76. Chaturvedi, R., Heimburg, J., Yan, J., Koury, S., Sajjad, M., Abdel-Nabi, H. H., and Rittenhouse-Olson, K. 2008. Tumor immunolocalization using 124 I-iodine-labeled JAA-F11 antibody to Thomsen-Friedenreich alpha-linked antigen. Appl Radiat Isot. 66:278-287.

77. Rittenhouse-Olson, K. 2008. Therapeutic use of anti-TF-antigen antibody. (USPTO) Pending Patent No. 20080226561.

78. Bian, C. F., Zhang, Y., Sun, H., Li, D. F., and Wang, D. C. 2011. Structural basis for distinct binding properties of the human galectins to Thomsen-Friedenreich antigen. PLoS One. 6:e25007.

79. Heimburg, J., Yan, J., Morey, S., Glinskii, O. V., Huxley, V. H., Wild, L., Klick, R., Roy, R., Glinsky, V. V., and Rittenhouse-Olson, K. 2006. Inhibition of spontaneous breast cancer metastasis by anti-Thomsen-Friedenreich antigen monoclonal antibody JAA-F11. Neoplasia. 8:939-948.

80. Roger, V. L., Go, A. S., Lloyd-Jones, D. M., Benjamin, E. J., Berry, J. D., Borden, W. B., Bravata, D. M., Dai, S., Ford, E. S., Fox, C. S., Fullerton, H. J., Gillespie, C., Hailpern, S. M., Heit, J. A., Howard, V. J., Kissela, B. M., Kittner, S. J., Lackland, D. T., Lichtman, J. H., Lisabeth, L. D., Makuc, D. M., Marcus, G. M., Marelli, A., Matchar, D. B., Moy, C. S., Mozaffarian, D., Mussolino, M. E., Nichol, G., Paynter, N. P., Soliman, E. Z., Sorlie, P. D., Sotoodehnia, N., Turan, T. N., Virani, S. S., Wong, N. D., Woo, D., Turner, M. B., and American Heart Association Statistics Committee and Stroke Statistics, S. 2012. Heart disease and stroke statistics—2012 update: a report from the American Heart Association. Circulation. 125:e2-e220.

81. Shah, R. V., Chen-Tournoux, A. A., Picard, M. H., van Kimmenade, R. R., and Januzzi, J. L. 2010. Galectin-3, cardiac structure and function, and long-term mortality in patients with acutely decompensated heart failure. Eur J Heart Fail. 12:826-832.

82. Tsai, T. H., Sung, P. H., Chang, L. T., Sun, C. K., Yeh, K. H., Chung, S. Y., Chua, S., Chen, Y. L., Wu, C. J., Chang, H. W., Ko, S. F., and Yip, H. K. 2012. Value and Level of Galectin-3 in Acute MI Patients Undergoing Primary Percutaneous Coronary Intervention. J Atheroscler Thromb.

83. Lombardi, D., Di Lauro, V., Piani, B., Scuderi, C., Spazzapan, S., Magri, M. D., Crivellari, D., Annunziata, M. A., De Cicco, M., and Veronesi, A. 2003. Acceptance of external infusion pumps in patients with advanced breast cancer receiving continuous infusion fluorouracil. Tumori. 89:488-491.

84. Burton, S. A., Ng, C. Y., Simmers, R., Moeckly, C., Brandwein, D., Gilbert, T., Johnson, N., Brown, K., Alston, T., Prochnow, G., Siebenaler, K., and Hansen, K. 2011. Rapid intradermal delivery of liquid formulations using a hollow microstructured array. Pharm Res. 28:31-40.

85. Bujak, M., Kweon, H. J., Chatila, K., Li, N., Taffet, G., and Frangogiannis, N. G. 2008. Aging-related defects are associated with adverse cardiac remodeling in a mouse model of reperfused MI. J Am Coll Cardiol. 51:1384-1392.

86. Jugdutt, B. I., and Jelani, A. 2008. Aging and defective healing, adverse remodeling, and blunted post-conditioning in the reperfused wounded heart. J Am Coll Cardiol. 51:1399-1403.

87. Jugdutt, B. I., Palaniyappan, A., Uwiera, R. R., and Idikio, H. 2009. Role of healing-specific-matricellular proteins and matrix metalloproteinases in age-related enhanced early remodeling after reperfused STEMI in dogs. Mol Cell Biochem. 322:25-36.

88. Leening, M. J., Elias-Smale, S. E., Felix, J. F., Kors, J. A., Deckers, J. W., Hofman, A., Stricker, B. H., and Witteman, J. C. 2010. Unrecognised MI and long-term risk of heart failure in the elderly: the Rotterdam Study. Heart. 96:1458-1462.

89. Dorr, M. 2010. Silent MI: the risk beyond the first admission. Heart. 96:1434-1435.

90. de Torbal, A., Boersma, E., Kors, J. A., van Herpen, G., Deckers, J. W., van der Kuip, D. A., Stricker, B. H., Hofman, A., and Witteman, J. C. 2006. Incidence of recognized and unrecognized MI in men and women aged 55 and older: the Rotterdam Study. Eur Heart J. 27:729-736.

91. Sheifer, S. E., Manolio, T. A., and Gersh, B. J. 2001. Unrecognized MI. Ann Intern Med. 135:801-811.

92. Lepur, A., Carlsson, M., Novak, R., Dumic, J., Nilsson, U., and Leffler, H. 2012. Galectin-3 endocytosis by carbohydrate independent and dependent pathways in different macrophage like cell types. Biochim Biophys Acta. 1820:804-818.

93. Moriki, T., Kuwabara, I., Liu, F. T., and Maruyama, I. N. 1999. Protein domain mapping by lambda phage display: the minimal lactose-binding domain of galectin-3. Biochem Biophys Res Commun. 265:291-296.

The invention claimed is:

1. A method of reducing fibrosis following myocardial infarction (MI) in a subject comprising administering to the subject an effective dose of Galectin-3C (Gal-3C), wherein the Gal-3C comprises the amino acid sequence of SEQ ID NO:3, wherein the Gal-3C has not been produced by enzymatic cleavage of a polypeptide comprising SEQ ID NO:1.

2. The method of claim 1, wherein the Gal-3C reduces excess collagen deposition in the heart.

3. The method of claim 1, wherein the Gal-3C improves the functionality of the heart.

4. The method of claim 1, wherein the subject is a human subject.

5. The method of claim 1, wherein the Gal-3C is administered beginning no less than 3 days post MI.

6. The method of claim 1, wherein the Gal-3C is administered beginning no less than 8 days post MI.

7. The method of claim 1, wherein the Gal-3C is administered beginning no less than 14 days post MI.

8. The method of claim 1, wherein the Gal-3C is administered beginning no less than 21 days post MI.

9. The method of claim 1, wherein the effective dose of Gal-3C is 0.15 mg/kg/day.

10. The method of claim 1, wherein the effective dose of Gal-3C is 0.3 mg/kg/day.

11. The method of claim 1, wherein the effective dose of Gal-3C is 0.5 mg/kg/day.

12. The method of claim 1, wherein the Gal-3C is administered intravenously, intramuscularly, transdermally, or subcutaneously.

13. The method of claim 1, wherein the Gal-3C is administered intravenously with a pump.

14. The method of claim 1, wherein the Gal-3C is administered in three divided doses.

15. The method of claim 1, wherein the Gal-3C is administered subcutaneously.

16. The method of claim 1, wherein the Gal-3C is produced by a nucleic acid encoding SEQ ID NO:3.

* * * * *